US011304927B2

(12) United States Patent
Chattopadhayay et al.

(10) Patent No.: US 11,304,927 B2
(45) Date of Patent: Apr. 19, 2022

(54) **BIOACTIVE EXTRACT, FRACTION OF *CASSIA OCCIDENTALIS* AND FORMULATION THEREOF FOR BONE REGENERATION**

(71) Applicant: COUNCIL OF SCIENTIFIC AND INDUSTRIAL RESEARCH, New Delhi (IN)

(72) Inventors: Naibedya Chattopadhayay, Uttar Pradesh (IN); Subhashis Pal, Uttar Pradesh (IN); Sudhir Kumar, Uttar Pradesh (IN); Ramakrishna Eppalapally, Uttar Pradesh (IN); Padam Kumar, Uttar Pradesh (IN); Sapana, Uttar Pradesh (IN); Jiaur Rahaman Gayen, Uttar Pradesh (IN); Riyazuddin Mohammed, Uttar Pradesh (IN); Sabyasachi Sanyal, Uttar Pradesh (IN); Anagha Gurjar, Uttar Pradesh (IN); Prabhat Ranjan Mishra, Uttar Pradesh (IN); Naresh Mittapelly, Uttar Pradesh (IN); Kamal Ram Arya, Uttar Pradesh (IN); Brijesh Kumar, Uttar Pradesh (IN); Srikanta Rath, Uttar Pradesh (IN); Arun Kumar Trivedi, Uttar Pradesh (IN); Maurya Rakesh, Uttar Pradesh (IN)

(73) Assignee: COUNCIL OF SCIENTIFIC AND INDUSTRIAL RESEARCH, New Delhi (IN)

(*) Notice: Subject to any disclaimer, the term of this patent is extended or adjusted under 35 U.S.C. 154(b) by 112 days.

(21) Appl. No.: 16/434,323

(22) Filed: Jun. 7, 2019

(65) Prior Publication Data
US 2019/0374504 A1 Dec. 12, 2019

(30) Foreign Application Priority Data

Jun. 8, 2018 (IN) .............................. 201811021504

(51) Int. Cl.
| | | |
|---|---|---|
| *A61K 31/353* | (2006.01) | |
| *A61K 36/482* | (2006.01) | |
| *A61P 19/08* | (2006.01) | |
| *A61K 47/44* | (2017.01) | |
| *A61K 31/7048* | (2006.01) | |

(52) U.S. Cl.
CPC ........ *A61K 31/353* (2013.01); *A61K 31/7048* (2013.01); *A61K 36/482* (2013.01); *A61K 47/44* (2013.01); *A61P 19/08* (2018.01)

(58) Field of Classification Search
None
See application file for complete search history.

(56) References Cited

U.S. PATENT DOCUMENTS

2006/0128610 A1* 6/2006 Cooper .................. A61P 25/22
514/16.4

OTHER PUBLICATIONS

Ahmad et al., "Phytochemical Evaluation and Bioactive Properties of Different Parts of Cassia Occidentals Plant Extracts," Asian Journal of Chemistry: vol. 25, No. 17, (2013), pp. 9945-9948.
Alakshmi et al., "Pharmacological Profile of *Cassia occidentalis* L—A Review," Academic Sciences, vol. 5, Issue 3, (2013), pp. 29-33.
Amin et al., "The Comparative Efficacy of Drug Therapies Used for the Management of Corticosteroid-Induced Osteoporosis: A Meta-Regression," Journal of Bone and Mineral Research, vol. 17, No. 8, (2002), pp. 1512-1526.
Bhat et al., "A Novel Keto Fatty Acid from Cassia Occidentalis Seed Oil," Fett/Lipid 98, vol. 98, (1996), pp. 176-177.
Bouvard et al., "Ultrastructural Characteristics of Glucocorticoid-Induced Osteoporosis," Osteoporosis Inst. vol. 20, (2009), pp. 1089-1092.
Canalis et al., "Glucocorticoid-Induced Osteoporosis: Path physiology and Therapy," Osteoporosis Int., vol. 18, (2007), pp. 1319-1328.
Carpinteri et al., "Glucocorticoide-Induced Osteoporosis and Parathyroid Hormone," J. Endocrinol Invest., (2010) 33 (7 Suppl): 9 pages.
Fraser et al., "Glucocorticoid-Induced Osteoporosis: Treatment Update and Review," Ther. Adv. Musculoskel Disease, No. 1(2), (2009), pp. 71-85.
Hatano et al., "C-Glycosidic Flavonoids from Cassia Occidentalis," Phytochemistry 52, (1999), pp. 1379-1383.
Kim et al., "Isolation of N-Methylmorpholine from the Seeds of *Cassia occidentalis* L." J. Agr. Food Chem., vol. 19, No. 1, (1971), pp. 198-199.
Kitanaka et al., "Two New Bitetrahydroanthracenes from Roots of *Cassia occidentalis* L." Chem. Pharm. Bull., vol. 37 (2), (1989), pp. 511-512.
Kitanaka et al., "Formation of Pigments by the Tissue Culture of Cassia Occidentalis," Chem. Pharm. Bull., No. 33 (3), (1985), pp. 971-974.
Kitanaka et al., "Studies on the Constituents of the Leaves of *Cassia torosa* Cav. L—The Structures of Two New C-Glycosylflavones," Chem. Pharm. Bull., vol. 37 (9), (1989), pp. 2441-2444.
Klein, "The Effect of Glucocorticoids on Bone and Muscle," Osteoporos Sarcopenia, vol. 1(1), (2015), pp. 39-45.
Kling et al., "Osteoporosis Prevention, Screening, and Treatment: A Review," Journal of Women's Health, vol. 23, No. 7, (2014), pp. 563-572.
Ko et al., "Production of Polyketide Pigments in Hairy Root Cultures of Cassia Plants," Chem. Pharm. Bull., vol. 43, No. 2, (1995), pp. 274-278.

(Continued)

*Primary Examiner* — Terry A Mckelvey
*Assistant Examiner* — Catheryne Chen
(74) *Attorney, Agent, or Firm* — Cantor Colburn LLP

(57) ABSTRACT

The present invention relates to a bioactive extract, fraction of *Cassia occidentalis* and formulation thereof for bone regeneration and treatment of glucocorticoid induced musculo-skeletal diseases and associated electrolyte imbalances.

16 Claims, 14 Drawing Sheets

(56) References Cited

OTHER PUBLICATIONS

Kumar et al., "Biphasic Calcium Phosphate-Casein Bone Graft Fortified With Cassia occidentalis for Bone Tissue Engineering and Regeneration," Bull. Mater. Sci, vol. 38, No. 1, (2015), pp. 259-266.
Lal et al., "Physcion and Phytosterol from the Roots of Cassia Occidentalis," Phytochemistry, vol. 12, (1973), p. 1186.
Li et al. "Cycloartane Triterpenoids from Cassia Occidentalis," Planta Med. vol. 78, (2012), pp. 821-827.
Li et al., "Anthraquinones and Lignans from Cassia Occidentalis," Helvetica Chimica Acta—vol. 93, (2010), pp. 1795-1802.
Muralles & Gaydou, "Composition en Acides Gras et en Sterols des Huiles Extraites des Graines de trois Cassia (Caesalpiniacees) d' origine senegalaise" vol. 33, No. 10, (1986), pp. 381-384.
O'Brien et al. "Glucocorticoids Act Directly on Osteoblasts and Osteocytes to Induce Their Apoptosis and Reduce Bone Formation and Strength," Endocrinology, vol. 145(4), (2004), pp. 1835-1841.
Panigrahi et al., "Activity Guided Chemo Toxic Profiling of Cassia Occidentalis (CO) Seeds: Detection of Toxic Compounds in Body Fluids of CO Exposed Patients and Experimental Rats," Chemical Research in Toxicology, vol. 28(6), (2015), pp. 1120-1132.
Pant & Singh "Amino-Acids of Some Wild Legumes," Curr. Science, vol. 9, (1969), pp. 213-214.
Purwar et al., "New Flavonoid Glycosides from Cassia Occidentalis," Indian Journal of Chemistry, vol. 42B, (2003), pp. 434-436.
Raie et al. "Alkanes and Alcohols in Cassia Seed Oil," Pak, J., Sci. Ind. Res., vol. 34, Nos. 7-8, (1991), pp. 285-287.
Rizvi et al., "Examination of a Phytosterolin and a Sterol from Cassia Plants," Phytochemistry, vol. 10, (1971), p. 670.
Sayyad et al., "Anthelmintic Activity of Ethanolic Extract of Cassia Occidentalis Linn." Int. Journal Pharm. Res. Sci, vol. 02 (1), (2014), pp. 42-46.
Schacke et al., "Mechanisms Involved in the Side Effects of Glucocorticoids," Pharmacology & Therapeutics, vol. 96, (2002), pp. 23-43.
Seeman, "Bone Modeling and Remodeling," Critical Reviews in Eukaryotic Gene Expression, vol. 19, Issue 3, (2009), p. 219, Abstract.
Singh et al., "Pharmacological and Phytochemical Profile of *Cassia occidentalis* L: A Review," Journal of Drug Delivery and Therapeutics, vol. 6(5), (2016), pp. 91-96.
Singh et al., "Two Flavonoid Glycosides from Cassia occidentalis Pods," Planta Medica, (1985), pp. 525-526.
Tiwari et al., "Anthraquinone Pigments from Cassia Occidentalis," Planta Medica vol. 32, (1977), pp. 375-377.
Tiwari et al., "Flavonoids from the Leaves of Cassia Occidentals," Phytochemistry, vol. 16, (1977), pp. 1107-1108.
Nader et al., "Chemical Investigation of Cassia occidentalis Linn. With Special Reference to Isolation of Xanthones from Cassis Species," Indian Journal of Chemistry, vol. 26, Section B, (1987), p. 703.
Yadava et al., "Chemical Constituents from Cassia Occidentalis Linn." Indian Journal of Chemistry, vol. 50B, (2011), pp. 1112-1118.
Yin et al., "Isolation and Structure Identification of Chemical Constituents from Cassia Occidentalis," vol. 33, (2013), No. 10, 3 pages. (Translation of Abstract Only).

\* cited by examiner

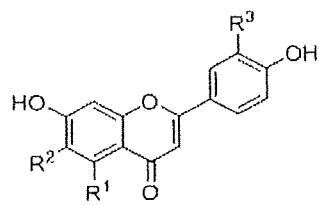

219/K007=4772/K012: R¹=OH, R²=R³=H, Apigenin
219/K009: R¹=R²=R³=H, 4',7-dihydroxyflavone
219/K010=4772/K015: R¹=R³=OH, R²=H, Luteolin
219/K011: R¹=R²=H, R³=OH, 3',4',7-trihydroxyflavone
219/K017=4772/K016: R¹=OH, R²=C-β-D-glucopyranoside, R³=H, Isovitexin
4772/K011: R¹=OH, R²=H, R³=OCH₃, Chrysoeriol

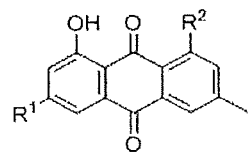

219/K012: R¹=R²=OH, Emodin
219/K014: R¹=H, R²=β-D-Gentiobioside, Chrysophanol-1-O-β-Gentiobioside
219/K015: R¹=O-β-Gentiobioside, R²=OH, Rhamnocathartin

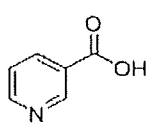

219/K013: Nicotinic acid

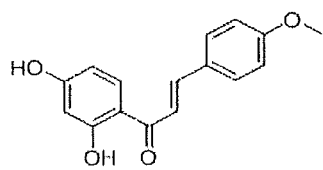

219/K008: 4-methoxy-2',4'-dihydroxy chalcone

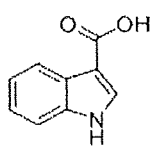

4772/K013: 1H-indole-3-carboxylic acid

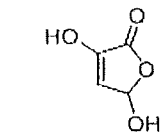

4772/K014: Pterospermin C

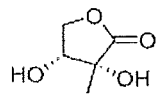

4772/K006: 2-C-Methyl-D-erythrono-1,4-lactone

FIGURE 4

BIOACTIVE EXTRACT, FRACTION OF *CASSIA OCCIDENTALIS* AND FORMULATION THEREOF FOR BONE REGENERATION

CROSS REFERENCE TO RELATED APPLICATIONS

This application claims priority to Indian Application No. 201811021504, filed Jun. 8, 2018, and all the benefits accruing therefrom under 35 U.S.C. § 119(b), the content of which is incorporated by reference in its entirety.

FIELD OF THE INVENTION

The present invention relates to a novel formulation for fracture healing and corticosteroid-induced musculo-skeletal diseases and associated electrolyte imbalances. Further it relates to the process of preparation of an extract and bioactive fraction from *Cassia occidentalis* stem and leaf, and a formulation thereof with enriched compounds for the treatment of glucocorticoid-induced musculo-skeletal disorders and promoting bone regeneration.

BACKGROUND OF INVENTION

Bone is an extremely specialized supporting frame-work of the body, characterized by its flexibility, hardness, and power of regeneration (achieved by bone modelling) and repair (achieved by bone remodeling). During childhood and adolescence, bone increases in size and mass to gain strength in order to adapt to the changing biomechanical forces. Fracture healing at any stage of life recapitulates the cellular events observed during bone growth (modeling). Bone remodeling on the other hand continues throughout the life to remove old and micro damaged bone by osteoclasts and replace it with new bone deposited by osteoblasts that is mechanically stronger to help preserve bone strength. In healthy bones, bone formation and resorption processes do not cause net bone gain or loss [Seeman E, Bone modeling and remodeling, Crit Rev Eukaryot Gene Expr. 2009; 19 (3):219-33]. Impairment in the function of the bone forming cells, osteoblasts is often a major cause of bone regeneration failure and is central to most of the metabolic bone diseases including osteoporosis [Juliana M. Kling, Bart L. Clarke and Nicole P. Sandhu, Osteoporosis Prevention, Screening, and Treatment: A Review, J Womens Health (Larchmt). 2014 Jul. 1; 23(7): 563-572.].

Glucocorticoid-induced osteoporosis (GIO) is the leading cause of medication-induced osteoporosis. In terms of skeletal safety, there is no "safe dose" of glucocorticoid.

Approximately 0.5% of the Indian population receives prolonged glucocorticoid therapy for various diseases and incidence of osteoporosis is 50% in these patients. The global prevalence of fractures in patients receiving long-term glucocorticoid stands at 30-50%.

Glucocorticoids are a class of steroid hormones and their synthetic forms (chemical modifications of natural glucocorticoids) are widely used to minimize symptoms in chronic inflammatory conditions such as allergy, asthma, arthritis, systemic lupus erythematosus, inflammatory bowel disease, autoimmune diseases and organ transplantation. In fact, synthetic glucocorticoid is the mainstay of anti-inflammatory and immunosuppressive therapy in the medical management of inflammatory states, and it has no substitute [Schacke, H., Docke, W. D., Asadullah, K., 2002. Mechanisms involved in the side effects of glucocorticoids. Pharmacol Ther 96, 23-43.]. Recipients of glucocorticoids could be from pediatric, adult or geriatric age.

Glucocorticoid therapy results in a rapid loss of bone mineral density, an important predictor of the risk of fracture. [Canalis, E., Mazziotti, G., Giustina, A., Bilezikian, J. P., 2007. Glucocorticoid-induced osteoporosis: pathophysiology and therapy. Osteoporoslnt 18, 1319-1328.]. The rate of bone loss is greatest in the first year of therapy and may be as high as 30% in the first six months [Bouvard, B., Audran, M., Legrand, E., Chappard, D., Ultrastructural characteristics of glucocorticoid-induced osteoporosis. Osteoporoslnt 20, 1089-1092]. This therapy is associated with fractures of the hip, spine, forearm and ribs, and substantially contributes to morbidity. Glucocorticoids shorten the lifespan of the bone forming cells, osteoblasts and thus reduce bone formation [O'Brien, C. A., Jia, D., Plotkin, L. I., Bellido, T., Powers, C. C., Stewart, S. A., Manolagas, S. C., Weinstein, R. S., 2004. Glucocorticoids act directly on osteoblasts and osteocytes to induce their apoptosis and reduce bone formation and strength. Endocrinology 145, 1835-1841]. In addition, chronic glucocorticoid treatment causes muscle wasting (sarcopenia) which is known to increase fracture risk [Gordon L. Klein, 2015 September, Osteoporosis and Sarcopenia, Vol 1, 39-45]. Furthermore, chronic glucocorticoid therapy causes electrolyte imbalance which could lead to hypertension and cardiovascular diseases. Glucocorticoids also adversely impact endocrine system causing insulin resistance and hyperparathyroidism due to altered calcium homeostasis.

The available therapy to protect from GIO is bisphosphonates which merely inhibit bone loss but do not increase bone formation [Amin, S., Lavalley, M. P., Simms, R. W., Felson, D. T., 2002. The comparative efficacy of drug therapies used for the management of corticosteroid-induced osteoporosis: a meta-regression. J Bone Miner Res 17, 1512-1526]. Rather, this drug class inhibits bone formation! In addition, high doses glucocorticoids cause osteonecrosis (inadequate blood supply to bone causing death of bone forming cells) and bisphosphonates have also been associated with osteonecrosis [Carpinteri, R., Porcelli, T., Mejia, C., Patelli, I., Bilezikian, J. P., Canalis, E., Angeli, A., Giustina, A., Mazziotti, G., Glucocorticoid-induced osteoporosis and parathyroid hormone. J Endocrinol Invest 33, 16-21]. Because the function of osteoblastic cells is particularly affected by glucocorticoids, the process of bone regeneration process which is dependent on healthy osteoblasts is affected in GIO. Bone regeneration is also impaired in other bone loss diseases such as post-menopausal osteoporosis.

A treatment that enhances bone formation (anabolic therapy) in GIO is an unmet medical need since the disease is primarily one of reduced bone formation. Furthermore, there is no therapeutic agent to prevent glucocorticoid-induced sarcopenia, electrolyte imbalance and endocrine disorders [Dr Lisa-Ann Fraser and Dr Jonathan D. Adachi, Glucocorticoid-Induced Osteoporosis: Treatment Update and Review, Ther Adv Musculoskelet Dis. 2009 April; 1(2): 71-85].

Previous Phytochemical Investigations

Phytochemical screening of *C. occidentalis* showed the presence of different class of compounds like flavonoids, saponins, anthraquinones, steroids, alkaloids, terpenes, glycosides, sterols and resins from different parts of *Cassia occidentalis* (Vijaylakshmi, S., Ranjitha, J., Devi Rajeshwari, V., Bhagiyalakshmi, M. International Journal of Pharmacy and Pharmaceutical Sciences 2013, 5, 29-33).

A number of anthraquinones and its derivative have been isolated from different parts of the plant. The compounds are characterized as aloe-emodin, emodin, rhein, physcion identified by GC-MS [Panigrahi, G. K., Ch, R., Mudiam, M. K. R., Vashishtha, V. M., Raisuddin, S., Das, M. Chem. Res. Toxicol. 2015, 28, 1120-1132], aurantio-obtusin, 1,4,11,12-tetrahydro-9,10-anthraquinone, [Lu, A.-h., Luo, X.-h., Zeng, J.-w., & Lin, Z.-n. Fujian NongyeXuebao 2012, 27, 422-426] identified by HPLC from seeds while germichrysone, cassiolin, 7-methylphyscion, 7-methyltorosachrysone [Kitanaka, S., Igarashi, H., Takido, M. Chem. Pharm. Bull. 1985, 33, 971-4] from callus, Xanthorin, helminthosporin, chrysophanol, 1,7-dihydroxy-3-methylxanthone, islandicin [Wader, G. R., Kudav, N. A. Indian J. Chem. 1987, Sect. B, 26B, 703], 8-O-methylchrysophanol, [Ko, K. S., Ebizuka, Y., Noguchi, H., Sankawa, U. Chem. Pharm. Bull. 1995, 43, 274-278.], 1-hydroxy-9,10-anthraquinone, diacerein, 1,8-dihydroxyanthraquinone [Alves, A. C. An. Fac. Farm. Porto 1964, 24, 65-119] and methylgermitorosone [Kitanaka, S., Takido, M. Chem. Pharm. Bull. 1989, 37, 511-12] from root, 1,8-dihydroxy-2-methylanthraquinone, isochrysophanol [Lal, J., Gupta, P. C. Experientia 1974, 30, 850-1] have been isolated from seeds. A number of combined anthracene derivative were also identified in different parts of plants i.e. glycosides of chrysophanol and emodin from leaves, glycosides of rhein and aloe emodin from roots, glycosides of chrysophanol and physcion from seeds [Rai, P. P., Shok, M. Indian J. Pharm. Sci. 1983, 45, 87-8].

Some bianthraquinone namely 5,7'-biphyscion [Yin, H.-q., Wei, J., Shang, B.-b., Zhang, Q.-s., Li, Y.-z. Beijing LigongDaxueXuebao 2013, 33, 1098-1100] from seeds, [1,1'-bianthracene]-4,4',5,5'-tetrahydroxy-2,2'-dimethyl-9,9',10,10'-tetrone [Tiwari, R. D., Singh, J. Planta Med. 1977, 32, 375-377] from leaves, singueanol-I, occidentalol-1, occidentalol-II [Kitanaka, S., Takido, M. Chem. Pharm. Bull. 1989, 37, 511-512], chrysophanol-10,10'-bianthrone [Kitanaka, S., Igarashi, H., Takido, M. Chem. Pharm. Bull. 1985, 33, 971-974] from root and anthraquinone glycoside like 6-O-(α-L-rhamnopyranosyl-(1→6)-β-D-glucopyranosyl)emodin [Li, S.-F., Di, Y.-T., Wang, Y.-H., Tan, C.-J., Fang, X., Zhang, Y., Zheng, Y.-T., Li, L., He, H.-P., Li, S.-L., et al. Helv. Chim. Acta 2010, 93, 1795-1802],1,3-dihydroxy-6,7,8-trimethoxy-2-methylanthraquinone-3-O-α-rhamnopyranosyl-(1→6)-β-glucopyranosyl(1→6)-β-galactopyranoside, 1-hydroxy-3,6,7,8-tetramethoxy-2-methylanthraquinone-1-O-α-rhamnopyranosyl (1→6)-β-glucopyranosyl(1→6)-β-galactopyranoside [Chauhan, D., Chauhan, J. S., Siddiqui, I. R., Singh, J. Indian J. Chem., Sect. B: Org. Chem. Incl. Med. Chem. 2001, 40B, 860-863] from leaves, physcion 8-043-D-glucopyranoside [Niranjan, G. S., Gupta, P. C. Planta Med. 1973, 23, 298-300] have been isolated from dried flowers of the plant.

The availability of flavonoids are mainly found in the ethanolic extract of whole plant. 4',7-dihydroxy-3-methoxyflavone, quertine, chrysoeriol-5-methyl ether, 3-O-methylfisetin, 3',4',7-trihydroxyflavone, 3-methylquercetin, (2S)-eriodictyol, 3'-methoxyapigenin, luteolin [Li, S.-F., Di, Y.-T., Luo, R.-H., Zheng, Y.-T., Wang, Y.-H., Fang, X., Zhang, Y., Li, L., He, H.-P., Li, S.-L. et al. Planta Med. 2012, 78, 821-827] have been isolated from whole plant, while apigenin [Anton, R., Duquenois, P. Ann. Pharm. Fr. 1968, 26, 673-680] and 4H-1-3,5,7-trihydroxy-2-(4-hydroxyphenyl)-benzopyran-4-one [Ahmad, I., Bashir, K., Mohammad, I. S., Wajid, M., Aziz, M. M. Asian J. Chem. 2013, 25, 9945-9948] have been isolated from dried roots and aerial parts. Flavonoid glycoside named apigenin-7-O-β-D-allopyranoside, 3,2'-dihydroxy-7,8,4'-trimethoxy-flavone-5-O-{β-D-glucopyranosyl(1→2)}-β-D-galactopyranoside [Purwar, C., Rai, R., Srivastava, N., Singh, J. Indian J. Chem., Sect. B: Org. Chem. Incl. Med. Chem. 2003, 42B, 434-436] from whole plant, matteucinol-7-rhamnoside, jaceidin-7-rhamnoside [Tiwari, R. D., Singh, J. Phytochemistry 1977, 16, 1107-1108] from ethanolic extract of leaves, cassia occidentalin C, cassia occidentalin B, cassia occidentalin A, torosaflavone B-3'-O-β-D-glucopyranoside [Hatano, T., Mizuta, S., Ito, H., Yoshida, T. Phytochemistry 1999, 52, 1379-1383] from aerial part, 3,5,3',4'-tetrahydroxy-7-methoxyflavone-3-O-(2''-rhamnosylglucoside),5,7,4'-trihydroxy-3,6,3'-trimethoxyflavone-7-O-(2''-rhamnosylglucoside) [Singh, M., Singh, J. Planta Med. 1985, 6, 525-526] from ethanolic extract of the pods, 5-[(O-α-L-arabinopyranosyl-(1→4)-O-6-deoxy-α-L-mannopyranosyl-(1→3)-β-D-galactopyranosyl)oxy]-2-(3,4-dihydroxyphenyl)-7-hydroxy-6-methoxy-4H-1-benzopyran-4-one, 3-[(6-deoxy-α-L-mannopyranosyl)oxy]-2-(3,4-dihydroxyphenyl)-7-[(3-O-β-D-glucopyranosyl-β-D-xylopyranosyl)oxy]-5-hydroxy-4H-1-benzopyran-4-one, 7-[[3-O-(6-deoxy-α-L-mannopyranosyl)-α-L-arabinopyranosyl]oxy]-2-phenyl-5-(β-D-xylopyranosyloxy)-4H-1-benzopyran-4-one, [Yadava, R. N., Satnami, D. K. Indian J. Chem., Sect. B: Org. Chem. Incl. Med. Chem. 2011, 50B, 1112-1118] have been isolated from seeds.

Two new cycloartanetriterpenoids, cycloccidentalic acids A and B and five related saponins, cycloccidentalisides I-V, Calonisterone, (+)-ajugasterone C, 20-hydroxy-α-ecdysone-3-acetate, 2-O-acetyl-20-hydroxyecdysone, poststerone along with chalconebutein and Robtein [Li, S.-F., Di, Y.-T., Luo, R.-H., Zheng, Y.-T., Wang, Y.-H., Fang, X., Zhang, Y., Li, L., He, H.-P., Li, S.-L., et al. Planta Med. 2012, 78, 821-827] have been isolated from whole plant.

Sesquilignans, seslignanoccidentaliol B, seslignanoccidentaliol A, threo-buddlenol C, erythro-buddlenol B, threo-buddlenol B, erythro-buddlenol C, hedyotisol A [Li, S.-F., Di, Y.-T., Wang, Y.-H., Tan, C.-J., Fang, X., Zhang, Y., Zheng, Y.-T., Li, L., He, H.-P., Li, S.-L. et al. Helv. Chim. Acta 2010, 93, 1795-1802] have been isolated from whole plant. Some steroids which are isolated from roots are □-sitosterol, (3β,24R)-ergost-5-en-3-ol, [Lal, J., Gupta, P. C. Phytochemistry 1973, 12, 1186](3β,24S)-stigmast-5-en-3-ol [Alves, A. C. An. Fac. Farm. Porto 1964, 24, 65-119], 28-isoavenasterol, 22-dihydrospinasterol, stigmasterolandcampesterol [Miralles, J., Gaydou, E. M. Rev. Fr. Corps Gras 1986, 33, 381-384] from seed oil. Besides these, some steroid glycosides named β-Sitosterol-α-glucoside and Campesterol-α-glucoside are also isolated from *Cassia occidentalis* seeds. [Rizvi, S. A. I., Lal, J., Gupta, P. C. Phytochemistry 1971, 10, 670].

The presence of several amino acids has been found in the seeds of this plant i.e. alanine, aspartic acid, glutamic acid, glycine, histidine, leucine-isoleucine, lysine, methionine, phenylalanine, proline, serine, threonine, tyrosine and valine. [Pant, R., Singh, K. S. Curr. Sci. 1969, 38, 213-214].

Some hydrocarbons (C18:0-C32:0) and alcohols (C12:0-C28:0) [Raie, M. Y., & Zaka, S. Pak. J. Sci. Ind. Res. 1991, 34, 285-287] as well as triglycerides and fatty acids [Zaka, S., Khan, S. A., & Akhtar, M. W. Proc. Pak. Acad. Sci. 1988, 25, 91-102] were also identified from seed oil of this plant.

Potassium chelidonate, 4-oxo-4H-Pyran-2,6-dicarboxylic acid, dipotassium salt was isolated from this plant. [Miyoshi, E., Shizuri, Y., & Yamamura, S. Chem. Lett. 1987, 3, 511-14]. Several volatile constituents from oil has been identified as 4,8-dimethyl-3,8-nonadien-2-one, 5-(1,2-dimethyl-1-propen-1-yl)-1,2,3-trimethyl-benzene, 7-methoxy-2,2-dimethyl-2H-1-benzothiopyran, 2-methyl-6-(4-methylene-2-cyclohexen-1-yl)-2-hepten-4-one, 2-ethylidene-1,1-dimethylcyclopentane, 3,5-octadien-2-one, 5-methoxy-6,7- dimethyl-benzofuran, 5-(1,1-dimethylethyl)-1,3-cyclopentadiene, (11Z)-11-tetradecen-1-ol, (3E,5E)-3,5-octadien-2-one, (1R,2R)-1-ethenyl-1-methyl-2-(1-methylethenyl)-4-(1-methylethylidene)-cyclohexane, 3,7-dimethyl-1,3-octadiene, octenal, (1S,5S)-6,6-dimethyl-2-methylene-bicyclo[3.1.1]heptanes, (1R,2R,5S)-2-methyl-5-(1-methylethyl)-bicyclo[3.1.0]hexan-2-ol, 4-(2,6,6-trimethyl-1-cyclohexen-1-yl)-2-butanone, (3E)-6-methyl-3,5-Heptadien-2-one, (3E,5Z)-6,10-dimethyl-3,5,9-undecatrien-2-one, 4-(2-buten-1-ylidene)-3,5,5-trimethyl-2-cyclohexen-1-one, 3,7,11-trimethyl-1-dodecanol, (4Z)-4-heptenal, 1-(4-methyl-3-cyclohexen-1-yl)-ethanone, (2R,5S)-5-ethenyltetrahydro-α,α,5-trimethyl-2-furanmethanol, 5-methyl-2-(1-methylethyl)-2-cyclohexen-1-one, (2E,4E)-2,4-heptadienal, (5E)-6,10-dimethyl-5,9-undecadien-2-one, 2-pentyl-furan, 2-methyl-5-(1-methylethyl)-bicyclo [3.1.0] hex-2-ene, 2,2,6-trimethyl-cyclohexanone, 1,3,5-cyclooctatriene, decahydro-1,6-dimethylnaphthalene, 6,10-dimethyl-2-undecanone, 1-tetradecene, (5E,9E)-6,10,14-trimethyl-5,9,13-pentadecatrien-2-one, decahydro-2,3-dimethylnaphthalene, 6-methyl-2-heptanone, 3-methylbenzaldehyde, 2,3-octanedione, 4-methyl-1-(1-methylethyl)-3-cyclohexen-1-ol, 1-methyl-2-(1-methylethyl)-benzene, (1R,2S,4R)-1,7,7-trimethylbicyclo[2.2.1]heptan-2-ol, 2-hexenal, 3,7,11,15-tetramethyl-1-hexadecen-3-ol, 6,10,14-trimethyl-2-pentadecanone, 2-methyl-5-(1-methylethyl)-phenol, 1,2,3,4-tetrahydro-1,1,6-trimethylnaphthalene, 2,6,6-trimethyl-1-cyclohexene-1-acetaldehyde, 2,6,6-trimethyl-1-cyclohexene-1-ethanol, 3,5,5-trimethyl-3-cyclohexen-1-one, (1R,4R)-1,7,7-trimethylbicyclo[2.2.1]heptan-2-one, 2,6,6-trimethyl-1-cyclohexene-1-carboxaldehyde, (2E,7R,11R)-3,7,11,15-tetramethyl-2-hexadecen-1-ol, (3S,6Z)-3,7,11-trimethyl-1,6,10-dodecatrien-3-ol, (2E)-3,7-dimethyl-2,6-octadienal, 6,10-dimethyl-3,5,9-undecatrien-2-one, 1-methyl-4-(1-methylethenyl)-cyclohexene, (3E)-4-(2,6,6-trimethyl-2-cyclohexen-1-yl)-3-buten-2-one, (1R,2R,4R)-rel-1,7,7-trimethylbicyclo[2.2.1]heptan-2-ol, 4-ethylphenol, benzeneacetaldehyde, 2,6,6-trimethyl-1,3-cyclohexadiene-1-carboxaldehyde, 2-undecanone, heptanal, 6-methyl-5-hepten-2-one, 2-heptanone, methylbenzene, 3,5-dimethylphenol, (2Z)-3,7-dimethyl-2,6-octadienal, 1-methoxy-4-(1-propen-1-yl)-benzene, benzaldehyde, 1-phenylethanone, α,α,4-trimethyl-3-cyclohexene-1-methanol, 5-(2-propen-1-yl)-1,3-benzodioxole, 1-phenyl-1-propanone, 1-butyl 2-octyl ester 1,2-benzenedicarboxylic acid, 2,6,6-trimethylbicyclo[3.1.1]hept-2-ene, (3E)-4-(2,6,6-trimethyl-1-cyclohexen-1-yl)-3-buten-2-one, 3,5,5-trimethyl-2-cyclohexen-1-one, (3R,3aS, 6R,7R,8aS)-octahydro-3,6,8,8-tetramethyl-,1H-3a,7-methanoazulen-6-ol [Li, M., Wang, Q.-r., Liu, J.-h., Huang, S.-j., Huo, X. Zhongguo Shiyan Fangjixue Zazhi (2013), 19, 122-126] by GC-MS.

A keto fatty acid, (Z)-7-oxo-,11-Octadecenoic acid have been isolated in appreciable amount from seed oil [Daulatabad, C. D., Bhat, G. G., Jamkhandi, A. M. Fett/Lipid 1996, 98, 176-177] and N-methylmorpholine was also isolated from seeds [Kim, H. L., Camp, B. J., Grigsby, R. D. J. Agr. Food Chem. 1971, 19, 198-199.].

Reference may be made to B SANTHOSH KUMAR, T HEMALATHA, R DEEPACHITRA, R NARASIMHA RAGHAVAN, P PRABU and T P SASTRY. Bull. Mater. Sci., Vol. 38, No. 1, February 2015, pp. 259-266 wherein Biphasic calcium phosphate-casein bone graft fortified with *Cassia occidentalis* for bone tissue engineering and regeneration are disclosed.

Objectives of the Invention

The main objective of the invention is to provide pharmaceutical formulation for bone regeneration and the treatment of musculo-skeletal diseases caused due glucocorticoid.

Another objective of the invention is to provide bioactive fractions, compounds and formulation of the fraction from the plant *Cassia occidentalis*.

Another object of the present invention is to provide the crude extract derived from *Cassia occidentalis* in pharmaceutically acceptable form.

Yet another object of the present invention is to provide the n-butanol soluble fraction derived from *Cassia occidentalis* in pharmaceutically acceptable form.

Still another object of the invention is to provide pure compounds apigenin and isovitexin from *Cassia occidentalis* in pharmaceutically acceptable form.

Yet another object of the invention is to provide a formulation of the ethanolic extract from *Cassia occidentalis*, in pharmaceutically acceptable form.

Still another object of the present invention is to provide a formulation of the butanolic fraction from *Cassia occidentalis*, in pharmaceutically acceptable form.

SUMMARY OF INVENTION

Accordingly present invention provides a pharmaceutical formulation for fracture healing and corticosteroid-induced musculo-skeletal diseases and associated electrolyte imbalances wherein the formulation comprising of *Cassia occidentalis* extract and/or bioactive fraction optionally along with pharmaceutically acceptable excipients wherein the extract/bioactive fraction containing marker compounds Apigenin 0.0005% to 0.002% and Isovitexin 0.0006% to 0.0008%.

In an embodiment of the present invention, the said pharmaceutical formulation comprising of:
i. alcoholic extract and/or fraction 2-10% w/w
ii. oil 20-60% w/w
iii. surfactant 20-40% w/w
iv. co-surfactant 12-28% w/w
v. solublizer 5-10% w/w.
vi. excipients (liquid to solid ratio) 10-60% w/w.

In an embodiment of the present invention, the oil used is selected from group comprising of, oleic acid, peanut oil, linoleic acid, soya bean oil or a combination thereof.

In an embodiment of the present invention, the surfactant and cosurfactant used is selected from group comprising Tween-80, labrafac, cemophor, Transcutol, caproyl 90, Tocopherol E succinate, Pluronic PF 127, propylene carbonate, polyethylene glycol and 1,2, ethanediol;

In an embodiment of the present invention, the solubilizer used is selected from group comprising poly ethylene glycol with different molecular weights ranging from 200-5000 glycerol, Labrasol™lauroglycol, soyalecithin, egg lecithin, cholic acid and deoxycholic acid, Soluplus®, Span 20 and Span 80.

In an embodiment of the present invention, excipients used are selected from group comprising polymers of sugars such as hypermellose, aerosil, HPMC, soluplus etc., inorganic materials such as colloidal silica, calcium carbonate, calcium phosphate etc.

Yet in another embodiment of the present invention, the process for preparation of the formulation comprising the following steps:

(a) percolating the powdered plant material with alcohol for a period ranging between 20 to 24 hrs followed by collecting the percolate, (b) repeating the step (a) for 4 to 5 times to obtain the alcoholic extract, (c) fractioning the alcoholic extract as obtained in step (b) with n-hexane to obtain hexane soluble fraction and hexane insoluble residue, (d) triturating the hexane insoluble residue as obtained in step (c) with ethylacetate to obtain ethylacetate soluble fraction and ethylacetate insoluble residue, (e) suspending the ethylacetate insoluble residue as obtained in step (d) with water followed by extracting with n-butanol to obtain n-butanol soluble fraction, (f) isolating Apigenin, 4-methoxy-2',4'-dihydroxy chalcone), 7,4'-dihydroxy flavone, Luteolin, 7,3',4'-trihydroxy-flavone, Emodin, Nicotinic acid, Chrysophanol 1-O-β-Gentiobioside, Rhamnocathartin, Isovitexin- from n-butanol soluble fraction as obtained in step (e) by chromatographic methods, (g) solubilizing Cassia extract/fraction obtained in step (b) or in step (e) with surfactant mixture under stirring to obtain nanoemulsion liquid preconcentrate formulation, (h) converting nanoemulsion liquid preconcentrate into solid system in situ by mixing with solid carrier wherein the ratio of liquid in-situ nanoemulsion system to solid carrier is from 1:0.5 to 1:10.

Yet in another embodiment of the present invention, the alcohol used is selected from ethanol or butanol.

Yet in another embodiment of the present invention, the surfactant mix consist of surfactant 20-40% w/w and co-surfactant 5-10% w/w.

Yet in another embodiment of the present invention, the solid carrier is selected from group comprising of HPMC, soluplus, colloidal silica, hypermellose and aerosil.

Yet another embodiment of the present invention provides the pharmaceutical formulation wherein the effective osteoinductive and skeletal preservation dose is reduced to 50 mg/kg in butanolic fraction formulation from 250 mg/kg in ethanolic extract.

Another embodiment of the present invention provides the pharmaceutical formulation wherein the effective muscle protective dose is reduced to 50 mg/kg in butanolic fraction formulation from 250 mg/kg in ethanolic extract.

Another embodiment of the present invention provides the pharmaceutical formulation wherein the relative bio-availability (as shown by AUC) of the apigenin 6-C-glucoside (biomarker) is enhanced by more than 5 fold as compared to the extract.

Yet in another embodiment of the present invention the compound isovitexin from ethanolic extract was more effective than apigenin in reversing osteopenia in mice as total bone volume and bone strength of femur were respectively 72% and 80% higher in isovitexin than apigenin treatment.

Yet in another embodiment of the present invention the butanolic fraction was more potent in bone regenerative effect than the ethanolic extract, as 100 mg/kg dose of butanolic fraction had equivalent osteoinduction parameters to that achieved by ethanolic extract at 250 mg/kg dose.

Yet in another embodiment of the present invention ethanolic extract formulation had greater bone regenerative effect than ethanolic extract.

Yet in another embodiment of the present invention butanolic fraction was more potent than ethanolic extract in preserving bone from MP-induced loss as 100 mg/kg dose of butanolic fraction had equivalent bone volume and bone strength parameters to that achieved by ethanolic extract at 250 mg/kg dose.

Yet in another embodiment of the present invention butanolic fraction formulation was more potent than ethanolic extract in preserving bone from MP-induced loss as 50 mg/kg dose of butanolic fraction formulation had equivalent bone volume and bone strength parameters to that achieved by butanolic extract at 100/kg dose.

Yet in another embodiment of the present invention butanolic fraction formulation was more potent in bone regenerative effect than butanolic fraction as 50 mg/kg dose of butanolic fraction formulation had equivalent increase in serum osteogenic marker to that achieved by butanolic fraction at 100 mg/kg dose.

BRIEF DESCRIPTION OF THE FIGURES

FIG. 4: Compounds isolated from Cassia occidentalis stem (CDRI plant code 219) and Cassia occidentalis leaves (CDRI plant code 4772)

ABBREVIATIONS

Figure 1:
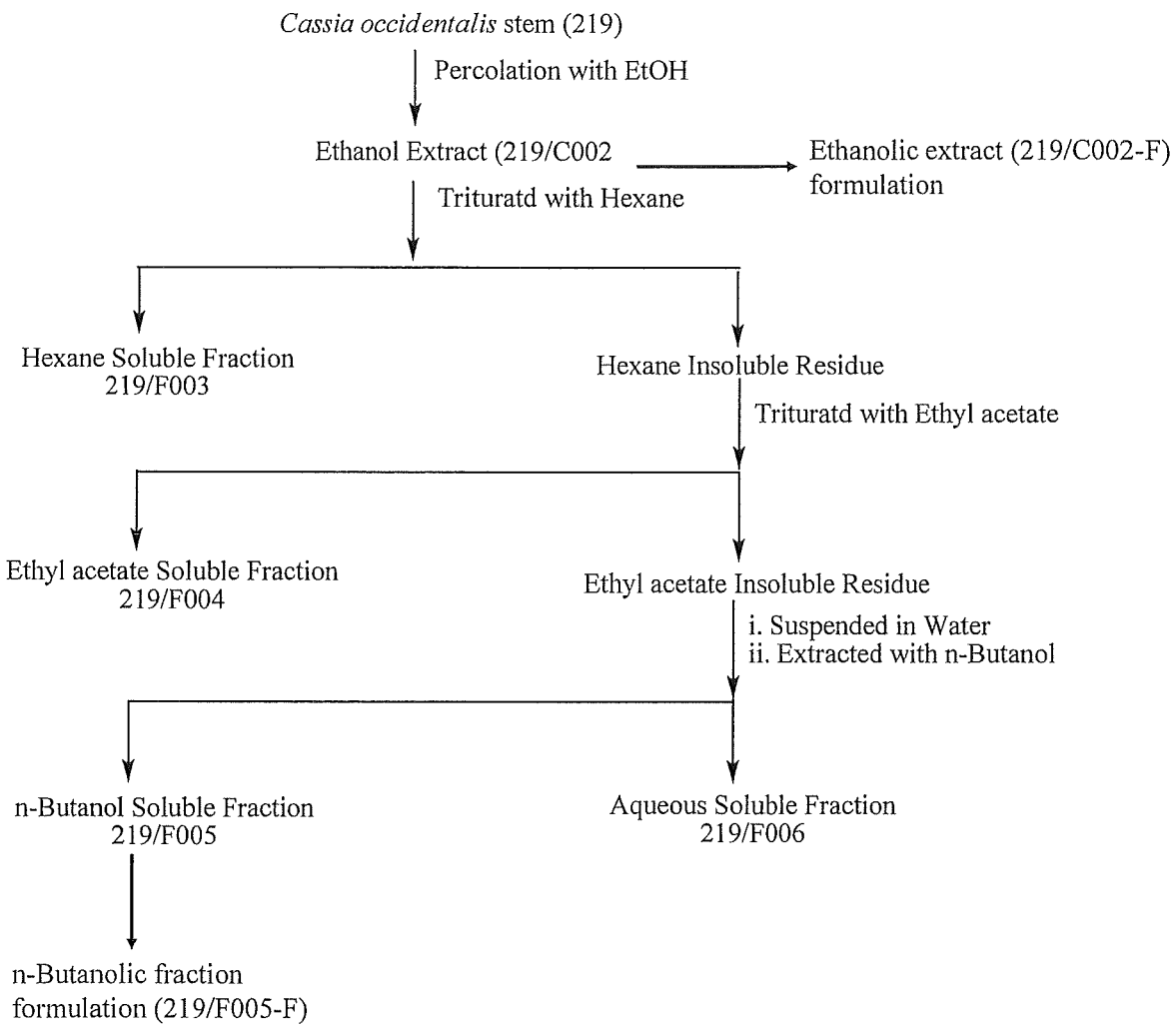
FIG. 1: Flow diagram showing extraction, formulation, isolation of extract from cassia occidentalis.

BMC—bone marrow stromal cells
OVX—ovariectomy
BMD—bone mineral density
RCO—Rat calvarial osteoblasts
M.P—Methylprednisolone
FBS—Fetal bovine serum
PBS—Phosphate Buffer Saline

DETAILED DESCRIPTION OF THE INVENTION

Accordingly, the present invention provides a pharmaceutical composition useful for the treatment of fracture healing and corticosteroid-induced musculo-skeletal diseases and associated electrolyte imbalances comprising of compounds of formula apigenin (219/K007) and apigenin-6-C-glycoside (219/K017),

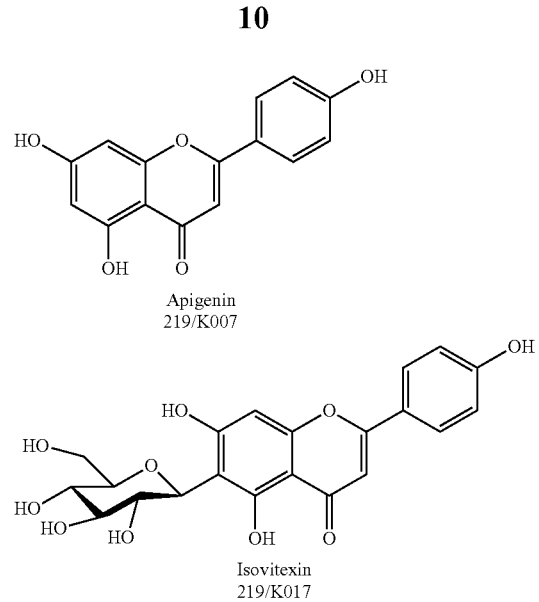

Apigenin
219/K007

Isovitexin
219/K017

2-10% W/W ethanolic/butanolic fraction of *Cassia occidentalis* extract(s); oil (20-60% W/W) comprising of peanut or linoleic acid or soya bean oil or a combination thereof; Surfactant 8 HLB-20-40% W/W comprising of Tween 80; co-surfactant—12-28% W/W comprising of 1, 2 ethanediol; Solubilizer—5-10% W/W comprising of PEG 1000.

Another embodiment of the invention provides abioactive fraction (219/F005) obtained from plant *Cassia occidentalis* stem/leaf wherein the fraction comprises; (219/F005: 1.50 to 1.70% with respect to dry *Cassia occidentalis* stem, 4772/F004: 1.1 to 1.4% with respect to dry *Cassia occidentalis* leaves).

Furthermore, another embodiment provides a compound 219/K017 from 219/C002 was significantly more effective than 219/K007 in reversing osteopenia in mice as total bone volume and bone strength of femur were respectively 72% and 80% higher in 219/K017 than 219/K07 treatment.

Another embodiment discloses, Compound 219/K017 (isovitexin) is in the range of 0.0006 to 0.0008%.

Even further, another embodiment provides the fraction 219/F005 was more potent in bone regenerative effect than the extract 219/, as 100 mg/kg dose of 219/F005 had equivalent osteoinduction parameters to that achieved by 219/C002 at 250 mg/kg dose.

Another embodiment discloses the fraction, 219/F005 was more potent than 219/C002 in preserving bone from MP-induced loss as 100 mg/kg dose of 219/F005 had equivalent bone volume and bone strength parameters to that achieved by 219/C002 at 250 mg/kg dose.

Further, another embodiment provides a process for preparation of bioactive fractions from plant *Cassia occidentalis* stem (plant 219), wherein the process steps comprising:
 (a) powdering the stems of the plant *Cassia occidentalis*;
 (b) percolating the powder as obtained in step (a) with alcohol for a period ranging between 20 to 24 hrs followed by collecting the percolate;
 (c) repeating the step (b) for 4 to 5 times to obtain the alcoholic extract 219/C002;
 (d) fractioning the alcoholic extract as obtained in step (c) with n-hexane to obtain hexane soluble fraction and hexane insoluble residue;
 (e) triturating the hexane insoluble residue as obtained in step (d) with ethylacetate to obtain ethylacetate soluble fraction and ethylacetate insoluble residue;

(f) suspending the ethylacetate insoluble residue as obtained in step (e) with water followed by extracting with n-butanol to obtain n-butanol soluble fraction 219/F005;

(g) isolating 10 compounds 219/K007 to 219/K015 and 219/K015, 219/K017 from fraction 219/F005 by chromatographic methods;

(h) Solubilizing *cassia* extract (2 to 10% w/w) obtained in step (e) in 75 to 150 mL of surfactant mixture to obtain the formulation; optionally dissolving the fraction (2 to 10% w/w) obtained in step (f) in 75 to 150 mL of surfactant mixture to obtain the formulation.

Furthermore, another embodiment provides the excipients used herein are polymers from sugars such as hypermellose, HPC etc. or inorganic materials such as colloidal silica. The ratio of liquid in-situ nanoemulsion system to solid carrier was from 1:0.5 to 1:10.

Furthermore, another embodiment provides the formulation wherein the relative bioavailability (as shown by AUC) of the apigenin 6-C-glucoside (biomarker) is enhanced by more than 5 fold as compared to the extract.

Furthermore, the formulation, 219/C002-F had significantly greater bone regenerative effect than 219/C002.

Furthermore, another embodiment discloses, the formulation, 219/F005-F was more potent in bone regenerative effect than 219/F005 as 50 mg/kg dose of 219/F005-F had equivalent increase in serum osteogenic marker to that achieved by 219/F005 at 100 mg/kg dose.

Furthermore, the formulation, 219/F005-F was more potent than 219/C002 in preserving bone from MP-induced loss as 50 mg/kg dose of 219/F005-F had equivalent bone volume and bone strength parameters to that achieved by 219/F005 at 100/kg dose.

Even furthermore, the formulation wherein the effective osteoinductive and skeletal preservation dose is reduced to 50 mg/kg in 219/F005-F from 250 mg/kg in 219/C002.

Furthermore, another embodiment discloses the formulation wherein the effective muscle protective dose is reduced to 50 mg/kg in 219/F005-F from 250 mg/kg in 219/C002.

Figure 2:
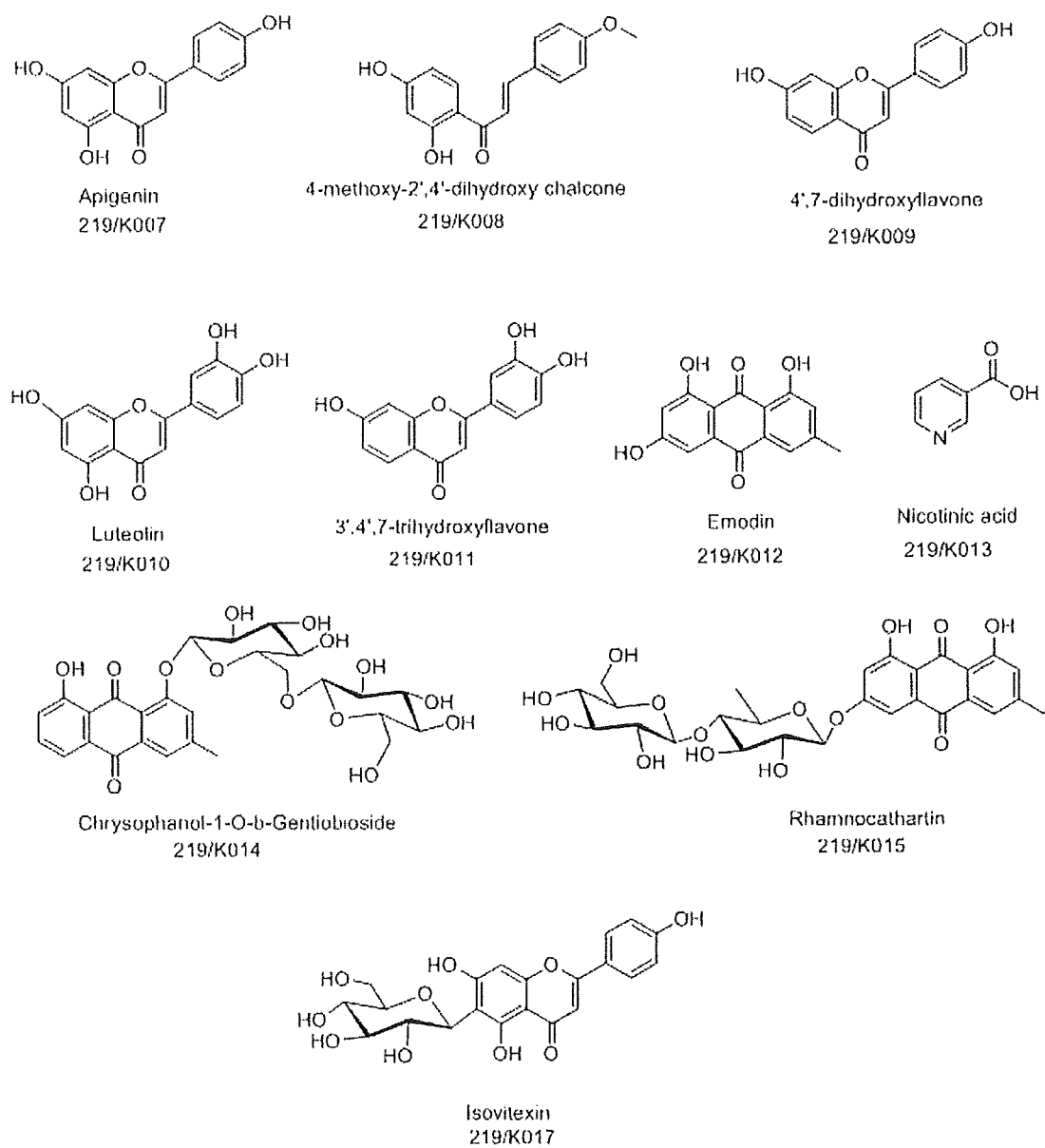
FIG. 2: Structure of compounds isolated from n-butanol soluble fraction (219/F005) of Cassia occidentalis stem

1. Isolation of compounds from n-butanol soluble fraction (219/F005) of *Cassia occidentalis* stems (FIG. 2 and FIG. 4)
    a) Apigenin (219/K007)
    b) 4-methoxy-2',4'-dihydroxy chalcone (219/K008)
    c) 7,4'-dihydroxy flavone (219/K009)
    d) Luteolin (219/K010)
    e) 7,3',4'-trihydroxy-flavone (219/K011)
    f) Emodin (219/K012)
    g) Nicotinic acid (219/K013)
    h) Chrysophanol 1-O-β-Gentiobioside (219/K014)
    i) Rhamnocathartin (219/K015)
    j) Isovitexin (219/K017)

Figure 3:
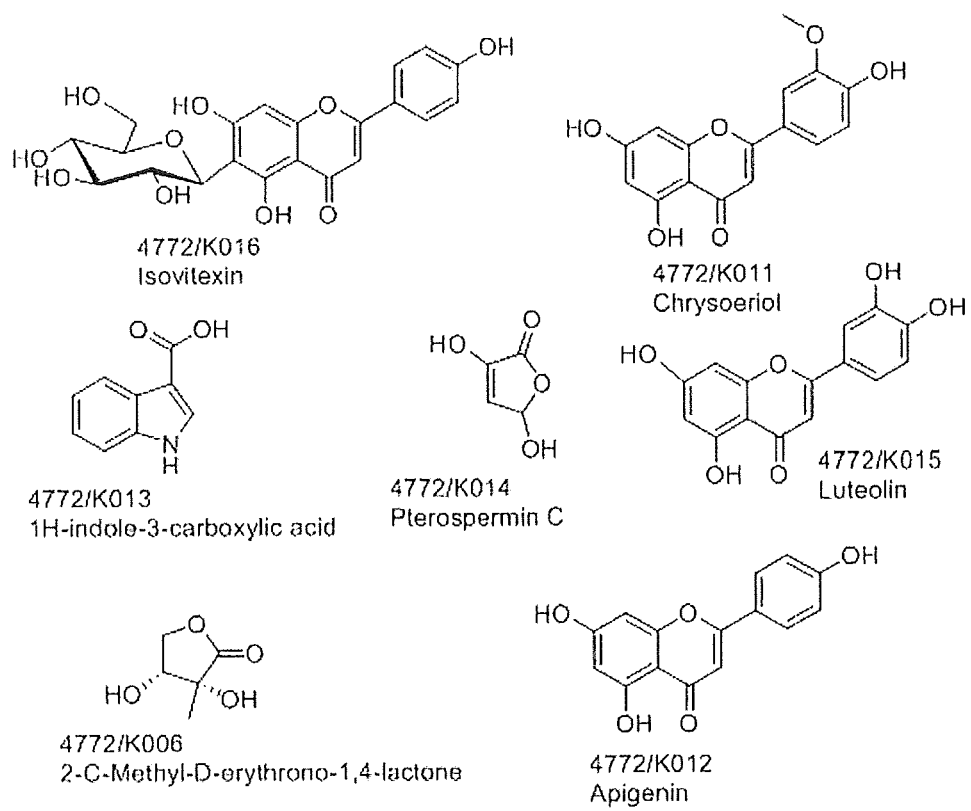
FIG. 3: Structure of compounds isolated from n-butanol soluble fraction (4772/F004) of Cassia occidentalis leaves.

2. Isolation of compounds from n-butanol soluble fraction (4772/F004) of *Cassia occidentalis* leaves (FIG. 3 and FIG. 4)
    a) 2-C-Methyl-D-erythrono-1,4-lactone (4772/K006)
    b) Chrysoeriol (4772/K011)
    c) Apigenin (4772/K012), identical with 219/K007 isolated from stem)
    d) 1H-indole-3-carboxylic acid (4772/K013)
    e) Pterospermin C (4772/K014)
    f) Luteolin (4772/K015), identical with 219/K010 isolated from stem)
    g) Isovitexin (4772/K016), identical with 219/K017 isolated from stem)

3. Amount of different component in *cassia* ethanolic extract were determined and it was found that active component Isovitexin/Apigenin C-glucoside content is 7.28 mg/g and Apigenin content is 1.95 mg/g.

TABLE 1

Principal Component Analysis of 219/C002 [Ethanolic extract of stem]

| | mg/g |
|---|---|
| Emodin | 0.50 |
| Chlorogenic acid | 0.38 |
| Ferulic acid | 0.8 |
| Protocatachuic acid | 1.28 |
| Apigenin | 1.95 |
| Kaempferol | 0.41 |
| Luteolin | 6.23 |
| Quercetin | 2.0 |
| 3',4',7-trihydroxyflavone | 58.4 |
| Isovitexin/apigeninC-glucoside | 7.28 |
| Rhamnocathartin | 0.61 |

Figure 5:
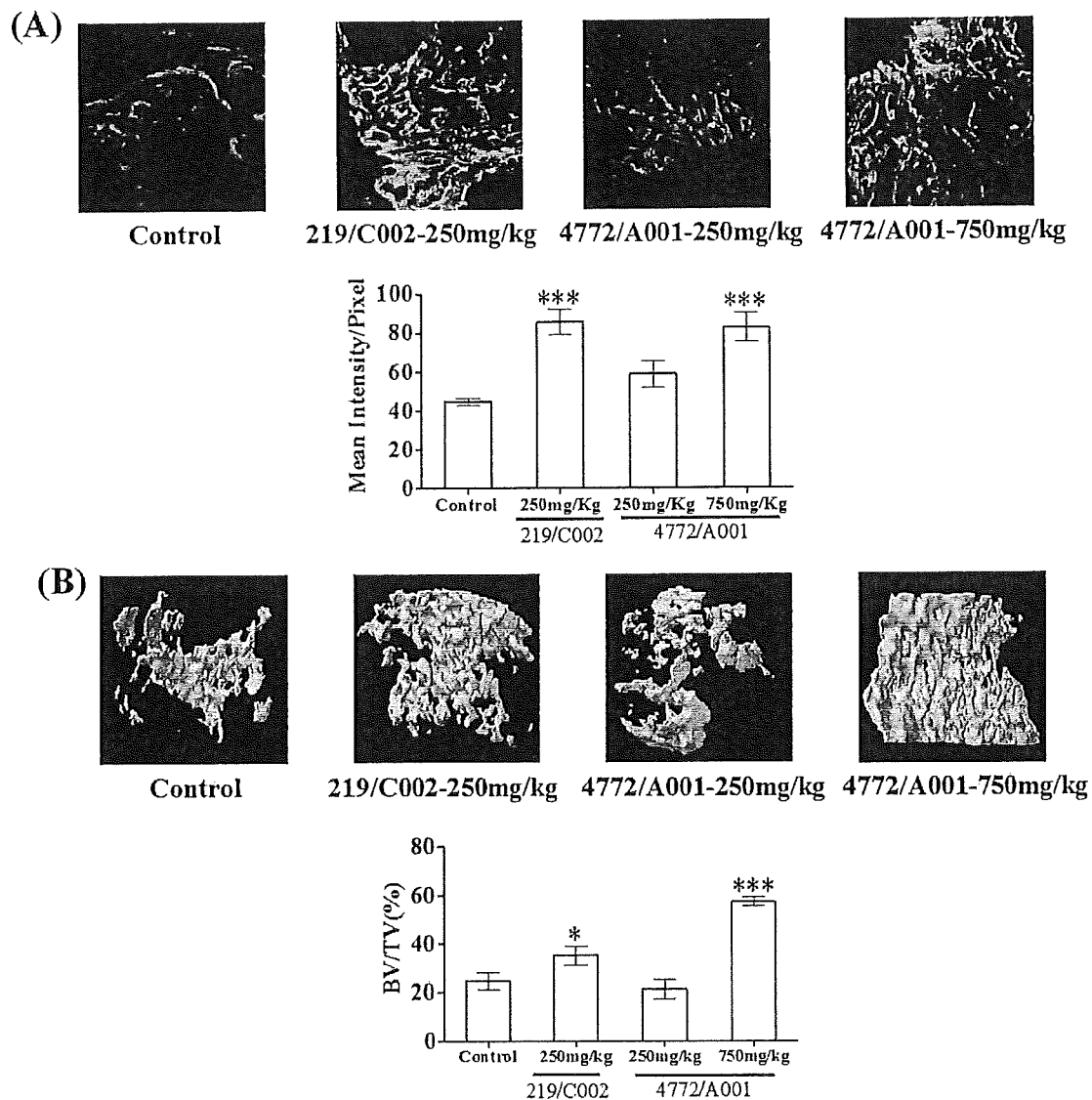
FIG. 5: 219/C002 and 4772/A001 (ethanolic extract of leaves) promoted new bone formation at fracture site. (A) 24 h after making a 0.8 mm drill-hole at femur diaphysis in adult female SD rats 219/C002 and 4772/A001 treatment at indicated doses were given for 12 d. Representative confocal images (10×) showing calcein deposition in callus in various groups (upper panel). Quantification of mean calcein intensity per pixel in the callus is shown in bottom panel. (B) Representative micro CT images showing new bone formation at fracture site (upper panel). Quantification of new bone (BV/TV) were measured by micro CT. Data are expressed as mean±SEM (n=10/group); *P<0.05, P<0.01 and *P<0.001 versus vehicle.

4. Two different fraction of ethanolic extract (219/C002, 4772/A001) were evaluated for new bone formation at fracture site. It was found that 219/C002 is active at 250 mg/Kg dose and 4772/A001 showed activity at 750 mg/kg dose. (FIG. 5)

Figure 6:
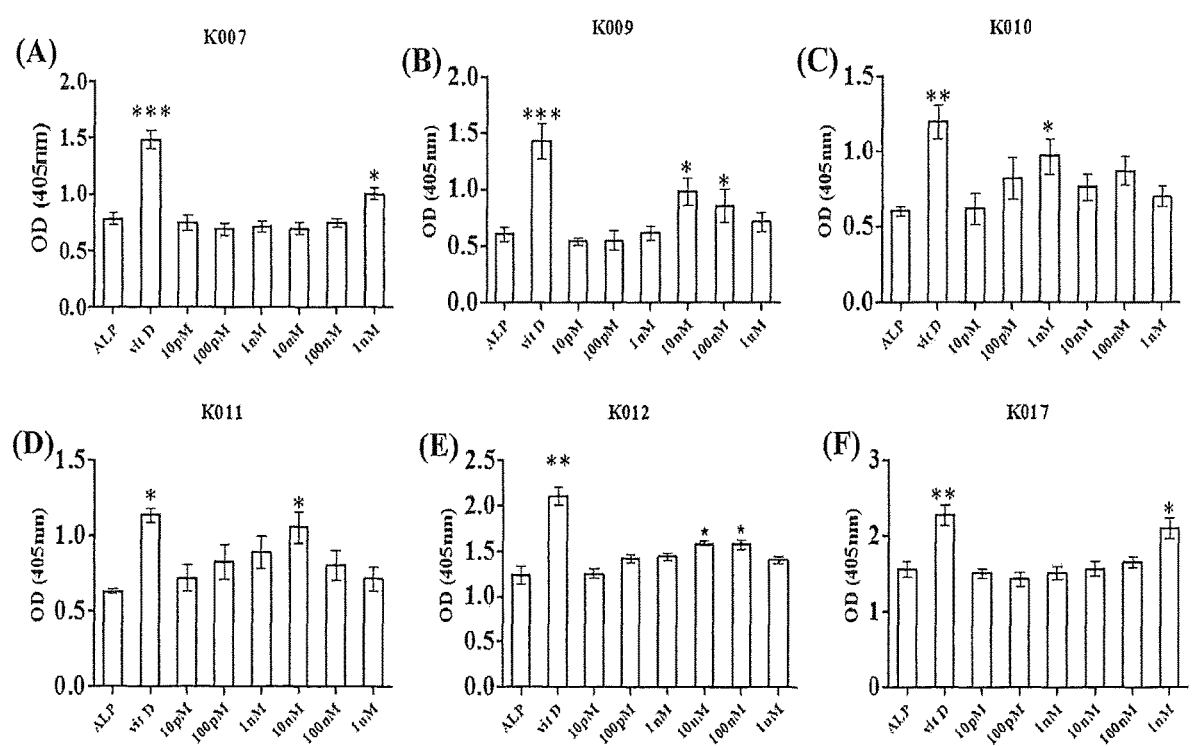
FIG. 6: 6 pure compounds of 219/C002 extract promoted osteoblast differentiation. Rat calvarial osteoblast were treated with different compounds at indicated concentrations for 48 h in differentiation medium and ALP activity was measured. 1,25 $(OH)_2$ vitamin D3 (10 nM) was used as positive control (6A-F). *P<0.05, P<0.01 and *P<0.001 signify changes in ALP activity compared with vehicle.

5. 10 different compounds were isolated from 219/C002 fraction and out of them 6 pure compounds of 219/C002 extract promoted osteoblast differentiation. (FIG. 6)

TABLE 2

List of pure compound isolated from 219/C002 and their osteogenic concentrations

| Name of the compound | Activity |
|---|---|
| 219/K007 | + (1 µM) |
| 219/K008 | − |
| 219/K009 | + (10 nM) |
| 219/K010 | + (1 nM) |
| 219/K011 | + (10 nM) |
| 219/K012 | + (10 nM) |
| 219/K013 | − |
| 219/K014 | − |
| 219/K015 | − |
| 219/K017 | + (1 µM) |

Figure 7:
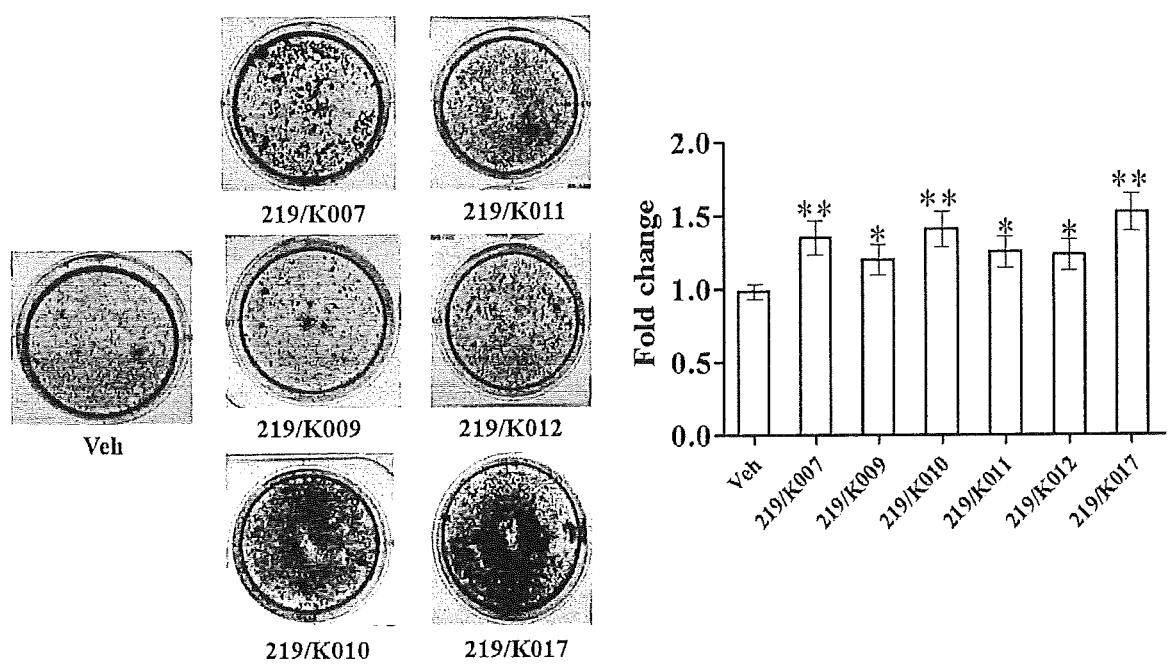
FIG. 7: 6 pure compounds of 219/C002 extract promoted osteoblast differentiation. BMSc were treated with different compounds at indicated concentrations for 21 days in differentiation medium and mineralized nodules were stained by Alizarine Red-S. *P<0.05 and **P<0.01 signify changes in mineralized nodule formation compared with vehicle.

6. Mineralization assay were performed by using 6 active component of the extract and all the compounds promoted mineralized nodule formation. (FIG. 7).

Figure 8:
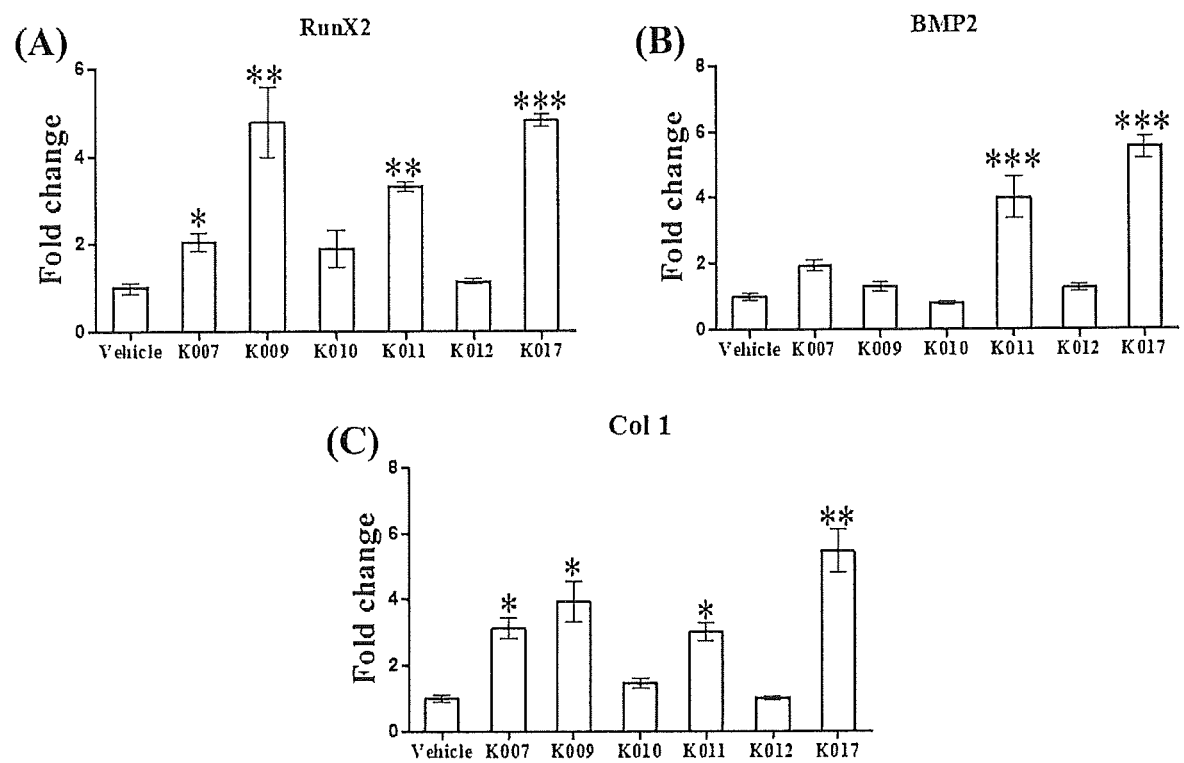
FIG. 8: K007, K009, K011 and K017 promoted osteogenic gene expression. Runx2, BMP2 and type 1 collagen (col1) mRNA levels determined by qPCR following 48 h incubation of Rat calvarial osteoblast with active concentration of the compounds (8A, 8B, 8C). *P<0.05, P<0.01, *P<0.001 compared with vehicle.

7. Osteogenic gene expression were measured and it was found that K007, K009, K011, K017 promoted RunX2 and Col1 expression. K011 and K017 promoted BMP2 expression. (FIG. 8)

Figure 9:
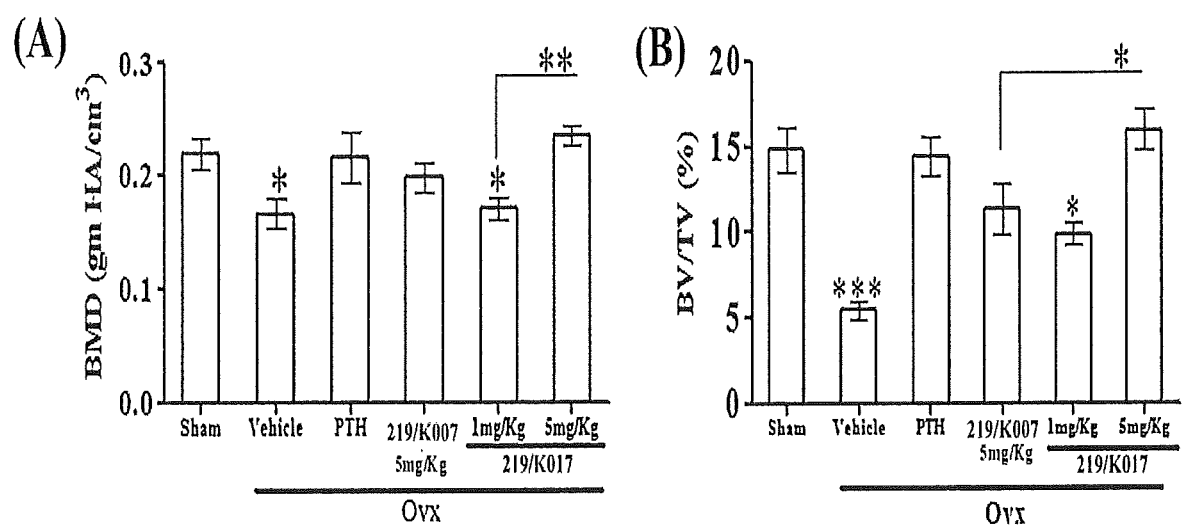
FIG. 9: 219/K017 completely restored femur trabecular microarchitecture in osteopenic mice. (A & B) Showing BMD and BV/TV of femur trabecular bone. Data are expressed as mean±SEM (n=10/group); *P<0.05, and **P<0.01 compared with vehicle.

8. 219/K017 completely restored femur trabecular microarchitecture in osteopenic mice at 5 mg/Kg dose and the effect was comparable with PTH, significantly better than 219/K007. (FIG. 9)

Figure 10:
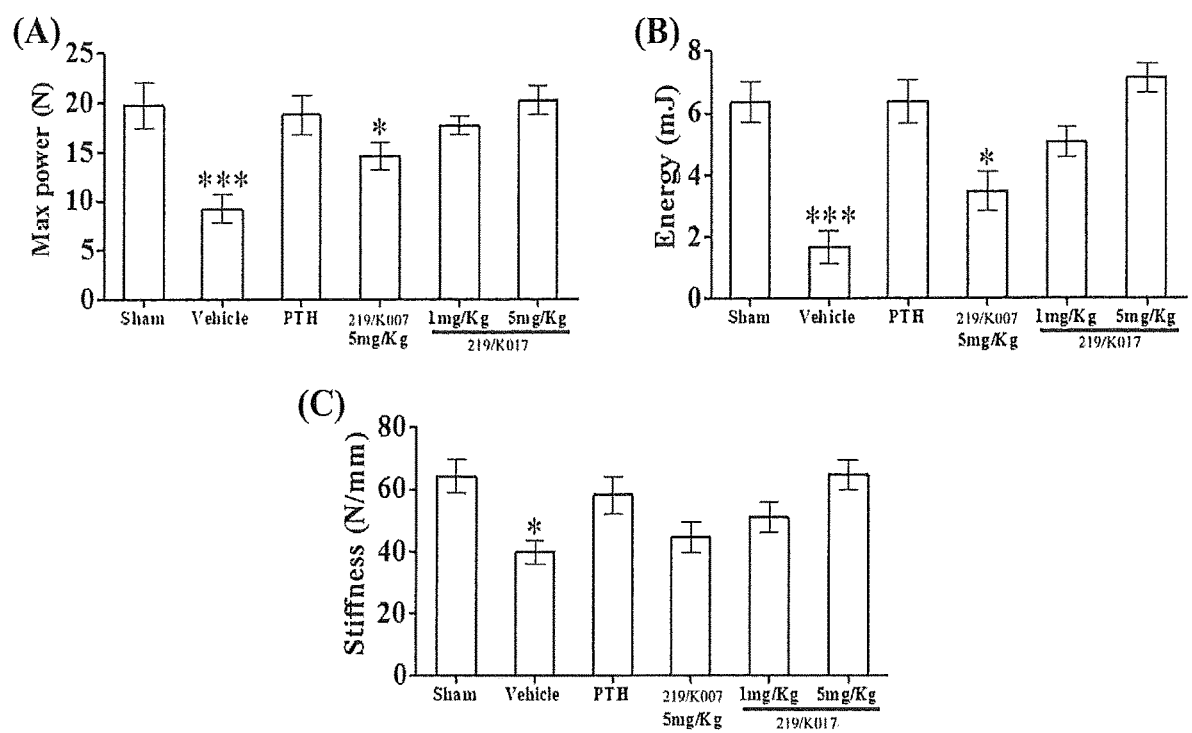
FIG. 10: 219/K017 restored femur cortical strength in osteopenic mice. Femur three-point bending was performed and maximum load to failure (A), stiffness (C) and energy (B) to failure were determined. Data are expressed as mean±SEM (n=10/group) *P<0.05 and ***P<0.001 compared to sham.

9. 219/K017 restored femur cortical strength in osteopenic mice, 219/K007 partially improve cortical strength in osteopenic animals. (FIG. 10) FIGS. 9&10 show that 219/K017 (isovitexin) is more potent than 219/K007 in improving bone health in osteopenic animals.

Figure 11:
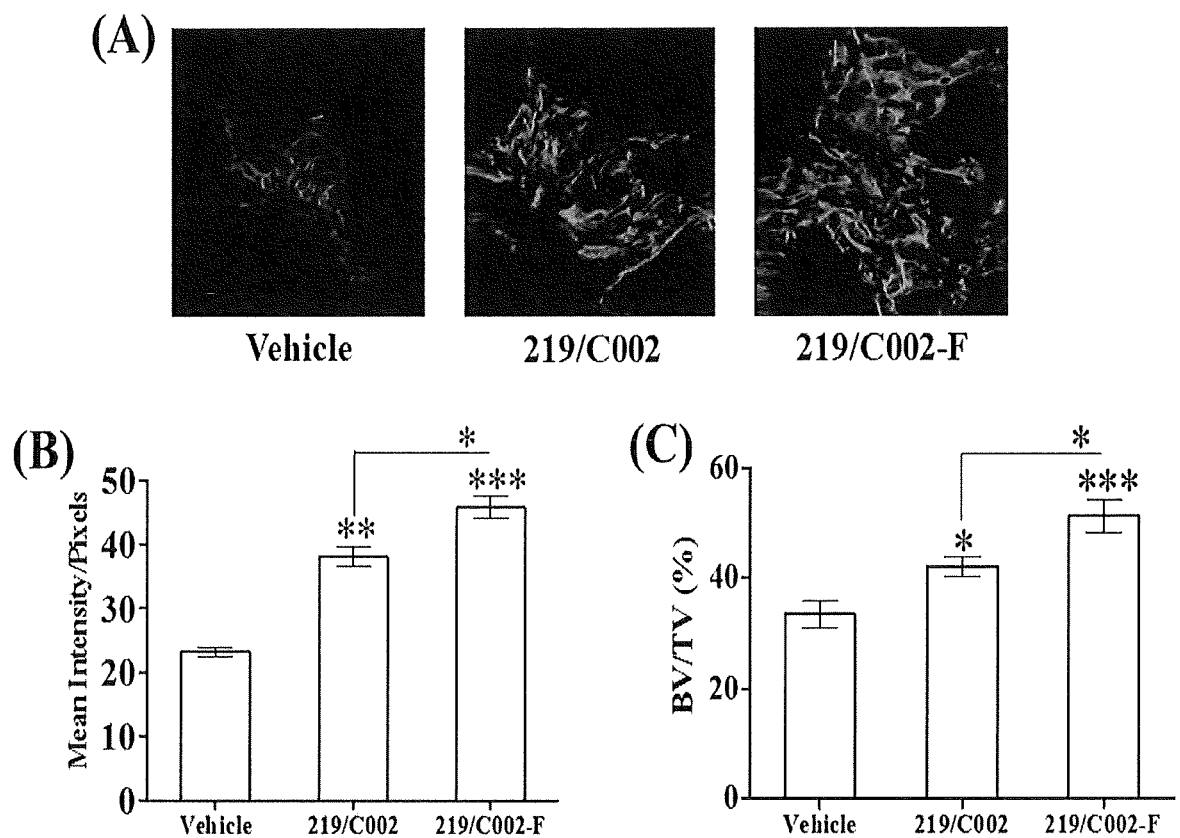
FIG. 11: 219/C002-F (ethanolic fraction formulation) have improved fracture healing capacity compared to 219/C002 (ethanolic fraction); both at 250 mg/kg dose. (A) Representative confocal images (10×) showing calcein deposition in callus in various groups. (B) Quantification of mean calcein intensity per pixel in the callus is shown in bottom panel. (C) Quantification of new bone (BV/TV) were measured by micro CT. Data are expressed as mean±SEM (n=10/group); *P<0.05, P<0.01 and *P<0.001 versus vehicle.

10. 219/C002 ethanolic fraction formulation (219/C002-F) improved fracture healing capacity as compared to the unformulated fraction. (FIG. 11) Pharmacokinetics of the formulated and unformulated fraction was compared and found that formulation robustly enhanced oral bioavailability of 219/K017. The Cmax and AUC of apigenin 6-C-glucoside (biomarker) increases significantly after formulation compared to the extract.

TABLE 3

Comparative PK of the unformulated and formulated fraction
Formulation contains excipients that are GRAS (generally recognized as safe) under
sections 201(s) and 409 of the Federal Food, Drug, and Cosmetic Act of U.S. FDA

|  |  | 219/K007 | | 219/K017 | |
| --- | --- | --- | --- | --- | --- |
|  | Oral dose | $C_{max}$ (ng/mL) | AUC (hr*ng/mL) | $C_{max}$ (ng/mL) | AUC (hr*ng/mL) |
| 219-C002 extract | 500 mg/kg | 0.93 ± 0.06 | 4.63 ± 2.34 | 0.15 ± 0.03 | 5.05 ± 0.57 |
| 219-C002 formulation | 500 mg/kg | 1.19 ± 1.37 | 5.65 ± 2.47 | 4.34 ± 1.55 | 26.21 ± 17.19 |

11. Fracture healing efficacy of 219/F005 (butanolic fraction) at 50 mg/kg and 100 mg/kg dose and found that 100 mg/kg was the effective dose. (FIG. 12) Butanolic fraction was 2.5 times more potent in osteogenic activity over the ethanolic fraction due to enrichment of the bioactive markers.

Figure 12:
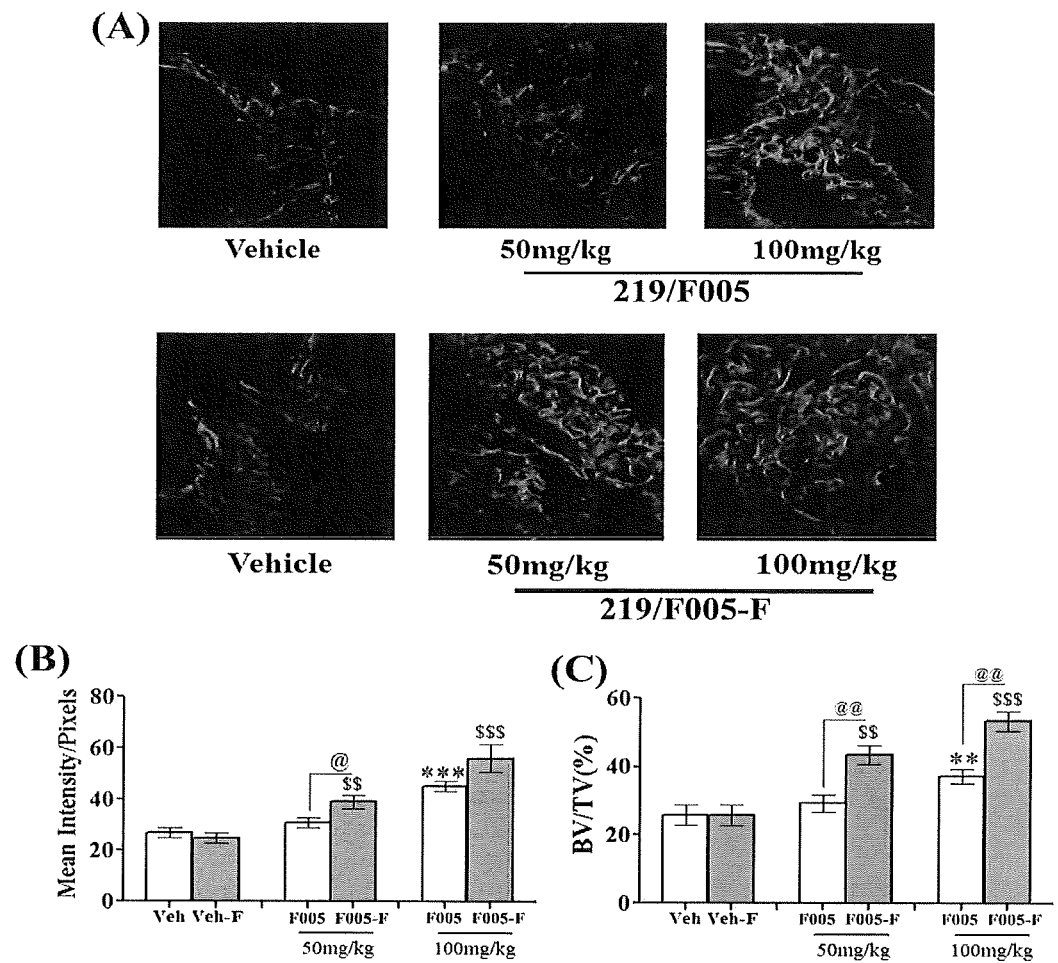
FIG. 12: 219/F005 (butanolic fraction) and 219/F005-F (butanolic fraction formulation) significantly enhanced new bone formation. 219/F005-F showed significantly better activity compared to 219/F005 in fracture model. (A) Representative confocal images (10×) showing calcein deposition in callus in various groups. (B) Quantification of mean calcein intensity per pixel in the callus is shown. (C) Quantification of new bone (BV/TV) were measured by micro CT. Data are expressed as mean±SEM (n=10/group); *P<0.05, P<0.01 and *P<0.001 versus vehicle (veh), $^{\$\$}$P<0.01 and $^{\$\$\$}$P<0.001 versus formulation vehicle (Veh-F), $^{@}$P<0.05, $^{@@}$P<0.01 showed comparison between formulation and unformulated fraction.

12. Data showed that formulation of butanolic fraction significantly increased osteogenic effect at 50 mg/kg dose whereas unformulated fraction showed efficacy only at 100 mg/kg (as shown in FIG. 12). From these data, it is evident that formulation enhanced osteogenic activity of not only ethanolic but also butanolic fraction. It is noteworthy that from 250 mg/kg dose in ethanolic extract, effective osteogenic dose is reduced to 50 mg/kg by formulating butanolic fraction.

13. Both ethanolic and butanolic fraction improves trabecular bone in MP treated animals. Butanolic fraction formulation improves the effectiveness of the extract. Improvement in cortical strength and serum PINP level after 1 month treatment was observed (Table 5). Overall data suggests that whereas 219/C002 (ethanolic fraction) could significantly mitigate MP-induced bone loss and reverse serum decreased serum osteogenic marker, P1NP, it is the butanolic fraction, and particularly the formulated butanolic fraction completely restored trabecular microarchitecture and serum PINP in MP treated animals.

TABLE 4

Comparative analysis among different fraction of Cassia extract for secondary osteoporosis.

| Parameter | Sham | MP | MP+ 219/C002 (250 mg/kg) | MP+ 219/F005 (100 mg/kg) | MP+ 219/F005-F (50 mg/kg) |
| --- | --- | --- | --- | --- | --- |
| BMD (gm-HA/cm$^3$) | 0.383 ± 0.016 | 0.281 ± 0.015** | 0.347 ± 0.012 | 0.342 ± 0.014 | 0.388 ± 0.021 |
| BV/TV (%) | 25.04 ± 1.32 | 18.33 ± 0.96*** | 21.66 ± 0.86*,[a] | 21.84 ± 0.77*,[b] | 24.21 ± 0.99 |
| Serum PINP (ng/ml) | 82.16 ± 3.02 | 50.17 ± 2.57*** | 69.09 ± 5.02*,[a] | 76.21 ± 5.86 | 77.18 ± 5.33 |
| Max power (N) | 119.01 ± 5.32 | 82.17 ± 3.77** | 93.5 ± 4.37*,[a] | 107.33 ± 3.56 | 119.33 ± 4.84 |
| Energy (mJ) | 121.35 ± 6.64 | 75.67 ± 3.48** | 98.2 ± 6.71*,[a] | 105.67 ± 6.01 | 116.33 ± 3.77 |
| Stiffness (N/mm) | 143.2 ± 7.27 | 108.17 ± 5.18** | 123.5 ± 3.81* | 124.5 ± 4.81 | 138.5 ± 5.17 |

Data are expressed as mean ± SEM (n = 10/group);
*P < 0.05,
**P < 0.01 and
***P < 0.001 versus vehicle.
[a]P < 0.05 and
[b]P < 0.01 versus MP.

Figure 13:
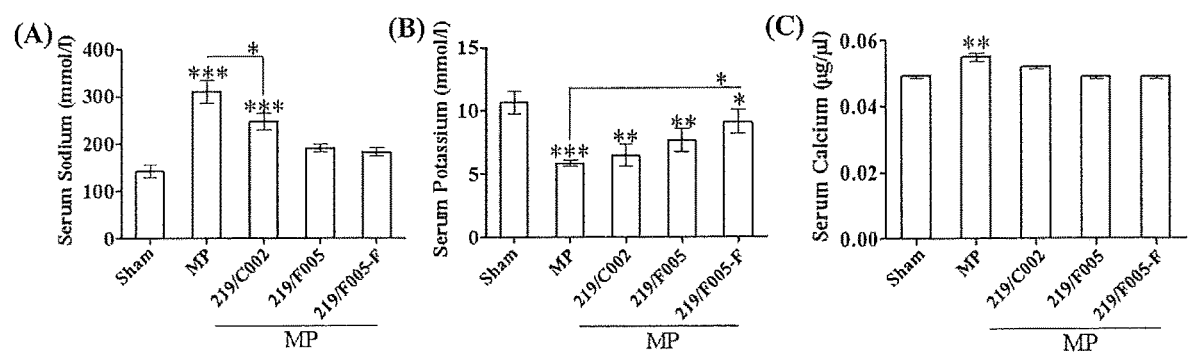
FIG. 13: *Cassia* extract improve serum electrolyte imbalance in MP treated animals (13A, 13B, 13C). 219/F005 and 219/F005-F completely restored serum sodium, calcium level and partially restore serum potassium level, whereas 219/C002 unable to restore serum Na, K level completely. Data are expressed as mean±SEM (n=10/group); *P<0.05, P <0.01 and *P<0.001 versus vehicle.

14. Serum electrolytes were measured and found that after MP treatment serum sodium level was increased and potassium level was decreased. 219/C002 (ethanolic fraction) could significantly mitigate changes in electrolyte and butanolic fraction (particularly formulation) completely restored serum sodium imbalance in MP treated animals. (FIG. 13).

Figure 14:
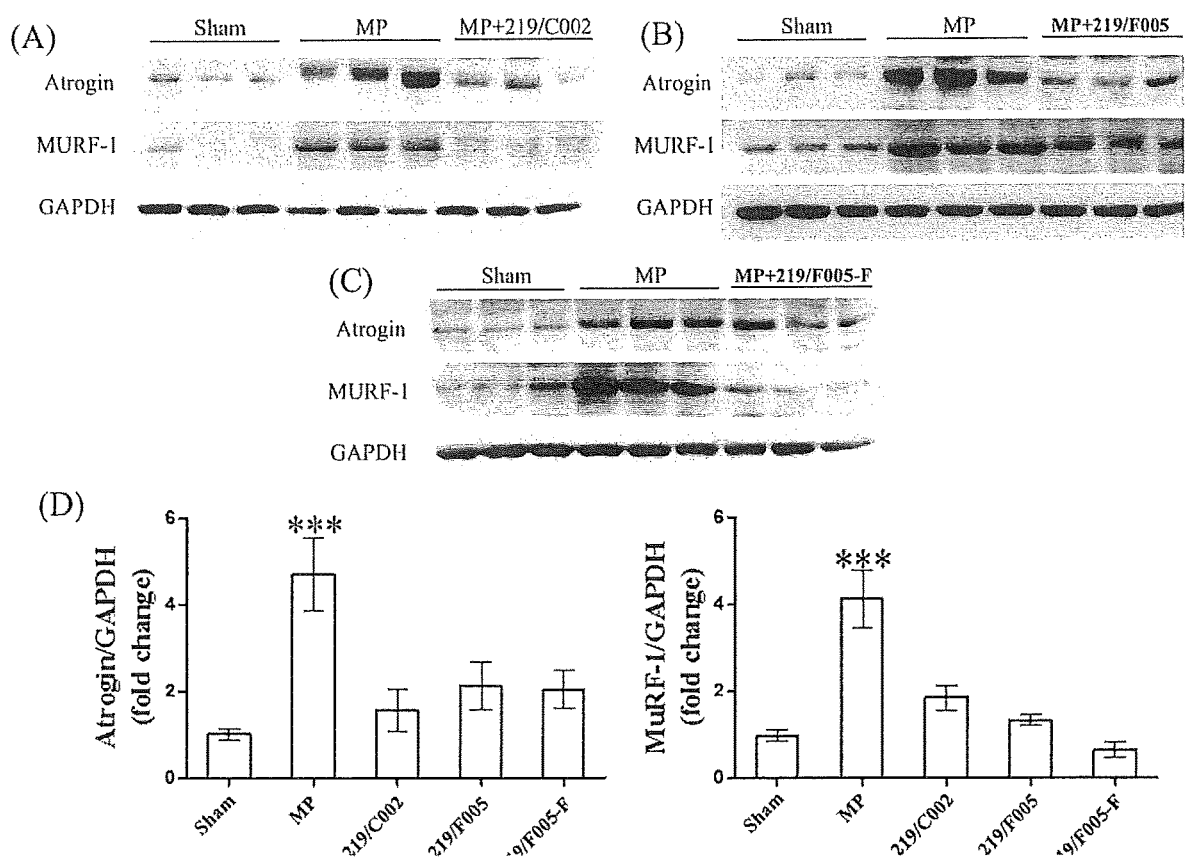
FIG. 14: *Cassia* extract lower muscle atrogin level in methylprednisolone treated animals. (14A, 14B, 14C) representative western blot of gastrocnemius muscle atrogin expression in different treatment group. (D) Quantification of relative atrogin and MURF-1 expression in different treatment group. Data are expressed as mean±SEM (n=3/group); ***P <0.001 versus vehicle.

15. Methylprednisolone treatment significantly enhanced muscle atrogin and murf-1 level after 1 month treatment. Cassia ethanolic, butanolic extract and butanolic formulation lower the muscle atrogin and murf-1 level. (FIG. 14).

EXAMPLES

The following examples are given by way of the illustration of the present invention and should not be construed to limit the scope of the present invention.

Example 1 Specifications of Raw Materials Used in the Extraction Process

*C. occidentalis* Linn. which is known as *Kaasaariin* Ayurveda, Kasondi in Hindi and Coffee Senna in English, belongs to Caesalpiniaceae family. It is an erect herb, commonly found by road sides, ditches and waste dumping sites throughout India. *C. occidentalis* is a common weed found throughout India (up to an altitude of 1500 m) from Jammu and Kashmir to Kanyakumari and used for a variety of purposes in indigenous, and folk medicines. The plant *C. occidentalis* was collected from Gram Panchayat, Raipur Raja VikasKhandBaksiKaTalab, Itaunza, Lucknow—226203 Uttar Pradesh. Plant species is abundantly available in the wild and collected from the surrounding areas of aforementioned geographical location (27.08080 N and 80.89590 E). Stem of the plant was separated and allowed to dry under shade. Ten kg each of dried stem (*Cassia occidentalis* stem, CDRI plant code No. 219) and leaves (*Cassia occidentalis* leaves, CDRI plant code No. 4772) was powdered prior to extraction.

Example 2

Preparation of Ethanolic Extract of *C. occidentalis* Stems (219/C002)

The powdered stem (10 kg) placed in a percolator with ethanol (35 L) and allowed to stand for about 24 h. The percolate was collected. This process of extraction was repeated 5×. The combined extract was filtered and concentrated under reduced pressure at 45° C. Weight of the extract obtained was 600.00 g (6% of 219/C002).

Example 3

Fractionation of Ethanolic Extract of *C. occidentalis* Stem

Ethanolic extract (600 g, 219/C002) of stem was triturated with hexane (500 ml×5). The n-hexane soluble fraction was concentrated under the reduced pressure at 40° C. Weight of hexane soluble fraction was 180 g (1.8% with respect to dry plant material, F003). The insoluble residue was triturated with ethylacetate (500 ml×4) and the ethylacetate soluble fraction was concentrated under reduced pressure at 40° C., that yielded 72 g (0.72% with respect to dry plant material, F004). Then ethylacetate insoluble residue was suspended into water (500 ml), extracted with n-butanol (300 ml×5). The combined n-butanol soluble fraction was concentrated under the reduced pressure at 45° C. and weight of n-butanol soluble fraction was 168 g (1.68% with respect to dry plant material, F005). The aqueous fraction obtained was 170 g (1.7% with respect to dry plant material, F006).

Example 4

Isolation of Compounds from n-Butanol Soluble Fraction (219/F005)

The n-butanol soluble fraction (219/F005, 168.0 g) was subjected to column chromatography over silica gel (1.5 kg, 60-120 mesh) eluted with a gradient solvent of chloroform-methanol (100:00, 95:05, 90:10, 85:15, 80:20, 75:25, 70:30, 60:40, 50:50) and finally eluted with methanol yielded fifty fractions (1000 ml each). On the basis of TLC profile, similar fractions were combined to give ten sub-fractions, F005A-F005J.

Sub-fraction F005B was subjected to column chromatography over a silica gel (230-400) using a gradient solvent system chloroform-methanol. On elution of column with chloroform-methanol (99;1) afforded yellow color solid (30 mg, 0.0003%, designated as 219/K007, identified as apigenin). On further elution of column with chloroform-methanol (98:2) afforded brick red colored solid compound (15 mg, 0.00015%, designated as 219/K008, identified as 4-methoxy-2',4'-dihydroxy chalcone) and elution with chloroform-methanol (95:5) afforded pale yellow colored solid compound (10 mg, 0.00010%, designated as 219/K009, identified as 7,4'-dihydroxy flavone).

Sub-fraction F005C was subjected to column chromatography over a silica gel (230-400) using a gradient solvent system chloroform-methanol. On elution of column with chloroform-methanol (95:5) afforded yellow solid compound (34 mg, 0.00034%, designated as 219/K010, identified as luteolin). On further elution of column with chloroform-methanol (94:6) afforded greenish yellow colored solid compound (8 mg, 0.00008%, designated as 219/K011, identified as 7, 3', 4'-trihydroxy-flavone).

Sub-fraction F005D was subjected to column chromatography using a chloroform-methanol with varying polarity. On elution of column with chloroform-methanol (92:8) afforded orange red colored compound (15 mg, 0.00015%, designated as 219/K012, identified as emodin) and further elution with chloroform-methanol (90:10) afforded brown solid (20 mg, 0.00020%, designated as 219/K013, identified as nicotinic acid).

Sub-fraction F005E was subjected to reverse phase chromatography over RP-18 by using varying amount of methanol in water as eluent system. On elution of column with water-methanol (75:25) afforded (4 mg, 0.00004%, designated as 219/K014, identified as chrysophanol 1-O-β-Gentiobioside) and on further elution of column with water-methanol (70:30) afforded (4 mg, 0.00004%, designated as 219/K015, identified as rhamnocathartin).

Sub-fraction F005F was subjected to reverse phase chromatography over RP-18 by using varying amount of methanol in water as eluent system. On elution of column with water-methanol (65:35) afforded (70 mg, 0.0007%, designated as 219/K017, identified as isovitexin).

Example 5

Preparation of Ethanolic Extract of *C. occidentalis* Leaves (4772/A001)

Powdered leaves of *C. occidentalis* (10 kg) were placed in percolator with ethanol (40 L) and allowed to stand at room temperature for about 24 hours. The percolate was collected. This process of extraction was repeated 5×. The combined extract was filtered and concentrated under reduced pressure at 45° C. Weight of extract was 700 g (yield 7%, designated as 4772/A001).

Example 6

Fractionation of Ethanolic Extract (4772/A001) of *C. occidentalis* Leaves

Ethanol extract (700 g) was triturated with hexane (500 ml×5). The hexane soluble fraction was then concentrated under the reduced pressure at 40° C., weight of hexane fraction obtained 300 g (3%, 4772/F002). The insoluble residue was triturated with ethylacetate (500 ml×4), the ethylacetate soluble fraction was concentrated under reduced pressure at 40° C., yielded 60 g (0.6%, with respect to dry plant material, 4772/F003). The insoluble residue was suspended in water (500 ml), extracted with n-butanol (250 ml×5). The n-butanol soluble fraction was concentrated under the reduced pressure at 45° C. Weight of n-butanol soluble and water soluble fraction was 120 g (1.2%, 4772/F004) and 200 g (2%, 4772/F005) respectively.

Example 7

Isolation of Compounds from n-Butanol Soluble Fraction (4772/F004)

The n-butanol soluble fraction (4772/F004, 120.0 g) was subjected to a column chromatography over silica gel (1.25 Kg, 60-120 mesh) eluted with gradient solvent of chloroform:methanol (100:00, 95:05, 90:10, 80:20, 75:25, 70:30, 50:50) and finally with methanol yielded forty fractions (1000 ml each). On the basis of TLC profile, similar fractions were combined to give seven sub-fractions F004A-F00G.

Sub-fraction F004A was subjected to column chromatography over silica gel (230-400) using gradient solvent system chloroform:methanol. On elution of column with chloroform:methanol (99:1) afforded white crystals (40 mg, 0.0004% designated as 4772/K006, identified as 2-C-Methyl-D-erythrono-1,4-lactone).

Sub-fraction F004B was subjected to column chromatography over silica gel (230-400) using gradient solvent system chloroform:methanol. On elution of column with chloroform:methanol (98:2) afforded white crystals (100 mg, 0.001% designated as 4772/K011, identified as chrysoeriol). On further elution of column with mixture of chloroform:methanol (98:02) afforded yellow solid (100 mg, 0.001% designated as 4772/K012, identified as apigenin, identical with 219/K007 isolated from stem).

Sub-fraction F004C was subjected to column chromatography over silica gel (230-400) using gradient solvent system chloroform:methanol. On elution of column with mixture of chloroform:methanol (95:05) to give white crystals (80 mg, 0.0008%, designated as 4772/K013, identified as 1H-indole-3-carboxylic acid).

Sub-fraction F004D was subjected to column chromatography over silica gel (230-400) using gradient solvent system chloroform:methanol. On elution of column with mixture of chloroform:methanol (96:4) to gave greenish powder (50 mg, 0.0005%, designated as 4772/K014, identified aspterospermin C).

Sub-fraction F004E was subjected to column chromatography over silica gel (230-400) using gradient solvent system chloroform:methanol. On elution of column with mixture of chloroform:methanol (95:5) to gave yellow crystals (40 mg, 0.0004%, designated as 4772/K015, identified as luteolin, identical with 219/K010 isolated from stem).

Sub-fraction F004F was subjected to reverse phase column chromatography over RP-18 silica gel using mixture of water:methanol solvent system. Elution of column with mixture of water:methanol (80:20) afforded pale yellow solid (300 mg, 0.003%, designated as 4772/K016, identified as isovitexin, identical with 219/K017 isolated from stem).

Example 8

Confirmation of Oral Absorption by Finger Printing
Instrument Used:
LC-MS/MS-API 4000 (Q-TRAP) triple quadrupole (AB-SCIEX, Toronto, Canada). The mass spectrometer was operated using an electrospray atmospheric pressure ionization source in positive ion mode.
a) Fingerprinting of 219/C002 Extract
Primary stock: 1 mg/mL in DMSO
Secondary stock: 50 ng/mL in Methanol
Continuous injection at 10 µL/min from secondary stock.
b) Fingerprinting of Blank Rat Plasma:
Blood was collected from overnight fasted rats and plasma was seperated. Plasma was precipitated with methanol (1:5 v/v), vortexed and centrifuged. The supernatant was collected and diluted with methanol (1:10 v/v). Continuous injection at 10 µL/min
c) Fingerprinting of 250 mg/kg (Oral) 219/C002 Treated Rat Plasma
Overnight fasted rats were administered 250 mg/kg 219/C002 extract suspension orally. Blood was collected after 45 min and plasma was separated. Plasma was precipitated with methanol (1:5 v/v), vortexed and centrifuged. The supernatant was collected and diluted with methanol (1:10 v/v). Continuous injection into the column at 10 µL/min.

Example 9

Rat Calvarial Osteoblasts (RCO) Culture

Calvaria from ten to twelve 1-2 day old rat pups were harvested, cleaned, and subjected to five sequential enzymatic digestions (0.1% diaspase and 0.1% collagenase I) of 10-15 min each. Cells from second to fifth digestion were collected, centrifuged, re-suspended and cultured in α-MEM containing 10% fetal bovine serum (FBS) and 1% penicillin/streptomycin (complete growth medium).

Example 10

Alkaline Phosphatase (ALP) Assay

For ALP assay, RCO were trypsinized at 80% confluence and $2 \times 10^3$ cells/well were seeded onto 24-well plates. Cells were treated with different compounds isolated from extract & vehicle for 48 h in α-MEM supplemented with 10 mM β-glycerophosphate, 50 mg/ml ascorbic acid and 1% penicillin/streptomycin (osteoblast differentiation medium).

At the end of the experiment, cells were washed with PBS, freeze fractured by placing the plates at −70° C. for 15 minutes followed by bringing to room temperature. ALP activity was measured by adding 100 µl p-nitrophenylphosphate buffer (2 mg/ml pNPP and 0.25 mM $MgCl_2$ in 1 M diethanolamine). The absorption was measured at 405 nm with a microplate reader.

Example 11

Mineralization of BMCs

The effect of active compounds on the mineralization of bone marrow stromal cells (BMCs), cells were harvested from the femurs of 3-month-old female rats (180 gm). Bone marrow was flushed out in 10 ml of osteoblast differentiation medium containing $10^{-7}$M dexamethasone (bone marrow differentiation medium). Released BMCs were collected and seeded ($4 \times 10^6$ cells/well) onto 12-well plates in bone marrow differentiation medium. BMCs were cultured with various compounds for 21 days at 37° C. in a humidified atmosphere of 5% $CO_2$ with change in medium every 48 h.

At the end of the experiment, cells were washed with PBS and fixed with 4% paraformaldehyde in PBS for 15 minutes. Calcium deposition by osteoblasts in the form of mineralized nodule was determined by alizarin red-S staining. Extraction of the stain was performed by 10% centylpyridiniumchloride (CPC) for colorimetric quantification at 595 nm.

Example 12

Quantitative real-time polymerase chain reaction (qPCR) was performed to determine the relative expressions of osteoblast and osteoclast specific genes in bones. GAPDH was used as the internal control. Primers were designed by the Universal ProbeLibrary (Roche Applied Science) for the following genes: RunX2, BMP2 and type 1 collagen (Col1). cDNA was synthesized with RevertAidcDNA synthesis kit (Fermentas, Austin, USA) using 2 µg total RNA. Relative mRNA levels of these genes was determined using a Light Cycler 480 through SYBR green chemistry (Roche Molecular Biochemicals, Indianapolis, USA).

Example 13

Drill-Hole Injury in the Femur:

A drill-hole was created in adult rats by inserting a drill bit with a diameter of 0.8 mm in the anterior portion of the diaphysis of femur, 2 cm above the knee joint. Treatments were given for 12 days prior to termination. 24 h before termination, calcein, a bone-seeking fluorochrome was administered to each rats (20 mg/kg, i.p.) to measure new bone formation at the fractured callus. On the $12^{th}$ day, rats were killed and femurs were collected and stored in 70% isopropanol for 48 h, and embedded in an acrylic material. Sections (60 µm) through the fracture callus were made using Isomet-Slow Speed Bone Cutter (Buehler, Lake Bluff, Ill.) followed by photography using confocal microscope (LSM 510 Meta, Carl Zeiss, Inc., Jena, Germany) with appropriate filters. The intensity of calcein binding was calculated using Carl Zeiss AM 4.2 image-analysis software.

Example 14

Osteopenic Mice Model:

50 adult female balb/c mice (20±3 g, 10-12 months) underwent either sham surgery or ovariectomy (OVX). 6 weeks post-surgery, mice were scanned using µCT to ensure development of osteopenia. Treatments of 219/K007 (5 mg/kg), 219/K017 (1 mg/kg and 5 mg/kg), PTH (40 µg/kg) and vehicle (water) were given to OVX mice with osteopenia for another 6 weeks, and vehicle treatment was given to sham operated mice for the same duration (n=10/group). After 6 weeks all mice were sacrificed and bones were collected for further experiment.

Example 15

MP induced secondary osteoporosis model:

50 adult male SD rats (260±20 g, 8-10 months) were divided into 5 groups. 5 mg/Kg methylprednisolone was administered subcutaneously for 1 month to induce osteoporosis. 219/C002 (250 mg/kg), 219/F005 (100 mg/Kg), 219/F005-F (50 mg/kg) treatment were given to check the efficacy of the extract and its different fraction along with methylprednisolone (n=10/group). After 1 month all rats were sacrificed and bones were collected for further experiment.

Example 16

CT Analysis:

A high-resolution X-ray micro-computed tomographic (µCT) for two-dimensional (2D) and three-dimensional (3D) assessment of bones (excised bones) were carried out using a Sky Scan 1076 µCT scanner (SkyScan, Ltd, Kartuizersweg, Kontich, Belgium). Briefly, after scanning bone samples at a nominal resolution (pixels) of 9 µm, cross-sectional reconstruction was made using SkyScanNrecon software based on a modified Feldkamp algorithm. To analyze trabecular bone, region of interest was drawn on a total of 100 slices in the region of secondary spongiosa situated 1.5 mm away from the distal border of growth plate (GP) excluding primary spongiosa and cortical bone. Quantification was done by employing Batman software encumbered with trabecular (3D) and cortical (2D) bone programs. Using µCT scans, trabecular bone mineral density (BMD) of femurs was determined from the volume of interest made for cortical and trabecular region, respectively. For calibration, hydroxyl apatite phantom rods of 4 mm of diameter with known BMD (0.25 $g/cm^3$ and 0.75 $g/cm^3$) were employed.

Example 17

Measurement of Bone-Turnover Markers:

Animals were kept in metabolic cages without food but with respective treatment and ad libitum water. Fasting serum samples were collected after 24 h. Serumprocollagen type I N-terminal propeptide (PINP) levels were determined by ELISA (MyBioSource, USA.), following the manufacturer's protocols.

Example 18

Three Point Bending Test:

Bone mechanical strength was examined by three-point bending of femur diaphysis with bone strength tester TK 252C (Muromachi Kikai Co. Ltd, Tokyo, Japan).

Example 19

Measurement of Muscle Atrophy

Gastrocnemius muscle samples were collected from each group and protein lysates were prepared to determine the levels of muscle atrogenes [atrogin 1, muscle ring finger protein (MuRF1)]. Relative expression of these proteins were detected by immunoblot analysis using specific antibodies, atrogin 1 (Abcam; 1:1000 dilution), MuRF1 (Santa Cruz Biotechnology; 1:1000 dilution) and GAPDH (Thermo Scientific; 1:1000 dilution). Densitometric analyses of immunoblots from three independent experiments were performed using ImageJ software.

Example 20

Measurement of Serum Cations:

Serum level of the $Na^+$ and $K^+$ were determined using Blood-Gas-Electrolyte MetaboliteAnalyser. Serum calcium was determined by a colorimetric kt (Sigma-Aldrich).

Example 21

Measurement of Biomarkers in Serum:

The mass spectrometer [LC-MS/MS-API 4000 (Q-TRAP) triple quadrupole (AB-SCIEX, Toronto, Canada)] was used for the assay. Overnight fasted rats were administered 250 mg/kg extract suspension orally. Blood was collected after 45 min and plasma was separated. Plasma was precipitated with methanol, vortexed and centrifuged. The supernatant was collected and diluted with methanol. Continuous injection at 10 µL/min was done for extract, blank plasma and extract treated plasma. 23 compounds were detected in extract and in extract-treated rat plasma but not in blank rat plasma. 5 out of 23 are known/ characterized molecule named Picolonic acid; 4',7-dihydroxyflavone; Apigenin; Luteolin; Apigenin 6-C-glucoside. This experiment confirms the oral absorption of biomarkers present in the extract.

Example 22

The nanoemulsion liquid preconcentrate formulation was prepared by mixing weighed quantity of *C. occidentalis* extract (219/C002)(2.5% W/W) with oleic acid (25 W/W), peanut oil (25% W/W), polysorbate 80 (25% W/W), and 1, 2 ethanediol (22.5% W/W). The mixture was stirred at 45.0 for 12 hr to obtain a clear dispersion. This formulation was stored at ambient temperature for further use.

Example 23

The nanoemulsion liquid preconcentrate formulation was prepared by dissolving weighed quantity of C. occidentalis extract (219/C002) (5% W/W) in the mixture of soya oil (55% W/W), Pluronic PF 127 (20% W/W), propylene carbonate (20% W/W) and poly ethylene glycol 1000. The mixture was kept on stirring at room temperature to get a clear solution. The formulation was stored at room temperature until further use.

Example 24

The nanoemulsion liquid preconcentrate formulation was prepared by mixing weighed quantity of C. occidentalis extract (219/C002) (10% W/W) in the mixture of oleic acid (50% W/W), vitamin E Tocopherol succinate poly ethylene glycol 1000 (2% W/W) and 1, 2 ethanediol 28% W/W. The mixture was stirred at ambient conditions to form a clear pre-concentrate. The formulation was stored until use ambient conditions.

Example 25

The nanoemulsion liquid preconcentrate formulation was prepared by mixing weighed quantity of C. occidentalis extract (219/C002) (10% W/W) in the mixture of Caproyl 90 (30% W/W), Cremophor EL® (25% W/W), Transcutol (30% W/W). The mixture was stirred for 24 hr at room temperature a get a clear solution and the formulation was stored at room temperature till further use.

Example 26

The nanoemulsion liquid preconcentrate formulation was prepared by mixing weighed quantity of C. occidentalis extract (219/C002) (10% W/W) in the mixture of Labrafac™ (45% W/W), polysorbate 80 (20%) and 1, 2 ethanediol (25% W/W). The mixture was stirred for 12 hr to obtain a clear solution. This formulation was stored at room temperature.

Example 27 (219/F005-F)

The nanoemulsion liquid preconcentrate formulation was prepared by mixing weighed quantity of C. occidentalis fraction (219/F005) (2% W/W) with peanut oil (25% W/W), oleic acid (25 W/W), polysorbate 80 (25% W/W), and 1, 2ethanediol (23% W/W). The mixture was stirred at 45.0 for 12 hr to obtain a clear dispersion. This formulation was stored at ambient temperature for further use.

Example 28 (219/F005-F)

The nanoemulsion liquid preconcentrate formulation was prepared by mixing weighed quantity of C. occidentalis fraction (219/F005) (10% W/W) in the mixture of oleic acid (50% W/W), 1, 2 ethanediol 28% W/W and vitamin E Tocopherol succinate poly ethylene glycol 1000 (2% W/W). The mixture was stirred at ambient conditions to form a clear pre-concentrate. The formulation was stored until use ambient conditions.

Example 29 (219/F005-F)

The nanoemulsion liquid preconcentrate formulation was prepared by mixing weighed quantity of C. occidentalis fraction (219/F005) (10% W/W) in the mixture of polysorbate 80 (20% W/W), Labrafac™ (45% W/W), and 1, 2ethanediol (25% W/W). The mixture was stirred for 12 hr to obtain a clear solution. This formulation was stored at room temperature.

Example 30

The nanoemulsion liquid preconcentrate was converted in to solid systems in situ by mixing Aerosil® in ethanol in 1:1 ratio with nanoemulsion liquid preconcentrate formulation followed by spray drying.

Example 31

The nanoemulsion liquid preconcentrate was converted in to solid systems in situ by mixing hypermellose containing water and ethanol (2:8 v/v) mixture with nanoemulsion liquid preconcentrate formulation in a 2:1 ratio followed by spray drying.

Example 32

The nanoemulsion liquid preconcentrate was converted in to solid systems in situ by mixing HPMC and Soluplus® in water and ethanol (2:8 v/v) and nanoemulsion liquid preconcentrate formulation in a 1:1 ratio followed by spray drying.

Example 33

LC-MS/MS method was developed for Biomarkers (apigenin and apigenin 6-C-glucoside) in negative ion mode for the oral PK studies.

Shimadzu HPLC apparatus consisted of LC-20AD binary pumps and SIL-HTcautosampler, (Shimadzu, Kyoto, Japan) was used to inject 10 µL aliquots of the processed samples on a Phenomenex Luna C18 column (4.6×150 mm, 5.0 µm). The system was run in isocratic mode with the mobile phase consisting of methanol and 10 mM ammonium acetate buffer in the ratio of 95:5 (v/v) at a flow rate of 0.6 mL/min. Mobile phase was duly filtered through 0.22 µm Millipore filter (Billerica, USA) and degassed ultrasonically for 15 min prior to use. Separations were performed at room temperature. Run time was for 4 min. Quercetin (50 ng/mL) was used as internal standard.

TABLE 7

LC-MS/MS method developed for Biomarkers (apigenin and apigenin 6-C-glucoside).

| Compound dependent parameters | Apigenin | Apigenin 6-C-glucoside | Quercetin (I.S) |
|---|---|---|---|
| Parent ion (m/z) | 269.3 | 431.2 | 301.2 |
| Daughter ion (m/z) | 116.9 | 311 | 151 |
| Dwell time (msec) | 150 | 150 | 150 |
| Declustering potential (V) | −76 | −100 | −76 |
| Entrance potential (V) | −10 | −10 | −10 |
| Collision energy (V) | −49 | −20 | −31 |
| Collision cell exit potential (V) | −5 | −31 | −10 |
| Source dependent parameters | | | |
| Ion source temperature (° C.) | | 500 | |
| Ion source gas 1 | | 50 | |
| Ion source gas 2 | | 50 | |
| Ion spray voltage (V) | | −4500 | |
| Collision gas | | 12 | |
| Curtain gas | | 30 | |

Rats were divided into two groups with six animals in each:

219-0002 extract—500 mg/kg
219-0002 formulation—500 mg/kg

Rats were administered respective dose after fasting for overnight. Blood samples were collected at 5, 15 min, 0.5, 1, 2, 4, 8, 12, 24, 48, and 72 hours. Plasma was separated and processed for analysis. Data was analyzed by WinNonlin software.

ADVANTAGES OF THE INVENTION i. *Cassia occidentalis* extract, fraction and formulation for bone regeneration
ii. Prevention for glucocorticoid-induced musculo-skeletal diseases caused due glucocorticoid
iii. Treatment for glucocorticoid-induced musculo-skeletal diseases

The invention claimed is:

1. A formulation for fracture healing and protection against corticosteroid-induced musculo-skeletal diseases, wherein the formulation comprises *Cassia occidentalis* extract and/or bioactive fraction optionally along with one or more pharmaceutically acceptable excipients, wherein the formulation comprises alcoholic extract and/or bioactive fraction in an amount ranging from 2-10% w/w, oil in an amount ranging from 20-60% w/w, surfactant in an amount ranging from 20-40% w/w, co-surfactant in an amount ranging from 12-28% w/w, solubilizer in an amount ranging from 5-10% w/w, and excipients in an amount ranging from 10-60% w/w.

2. The formulation as claimed in claim 1 wherein the oil is oleic acid, peanut oil, linoleic acid, soya bean oil, or a combination thereof.

3. The formulation as claimed in claim 1 wherein the surfactant and cosurfactant is polysorbate 80, polysorbate 20, polysorbate 60, medium-chain triglycerides of caprylic (C8) and capric (10) acids, polyoxyl 35 castor oil, diethylene glycol monoethyl ether, propylene glycol monocaprylate 90, tocopherol polyethylene glycol succinate (TPGS), poly(ethylene glycol)-block-poly(propylene glycol) (poloxamer 407), propylene carbonate, polyethylene glycol, or 1,2, ethanediol.

4. The formulation as claimed in claim 1 wherein the solubilizer is polyethylene glycol, with different molecular weights ranging from 200-5000, glycerol, caprylcaproyl macogol glycerides, lauroglycol, soya lecithin, egg lecithin, cholic acid and deoxycholic acid, polyvinyl caprolactam-polyvinyl acetate polyethylene glycol graft copolymer, sorbitan monolaurate 20, or sorbitan monolaurate 80.

5. The formulation as claimed in claim 1 wherein the one or more excipients are polymers of sugars or inorganic materials.

6. The formulation as claimed in claim 1 wherein the formulation is useful for treatment of fracture healing and corticosteroid-induced musculo-skeletal diseases and associated electrolyte imbalances.

7. A process for preparation of the formulation as claimed in claim 1 wherein the process comprises the steps of:
a. percolating powdered *Cassia occidentalis* plant material with alcohol for a period ranging between 20 to 24 hrs followed by collecting the percolate,
b. repeating the step (a) for 4 to 5 times to obtain the alcoholic extract,
c. fractioning the alcoholic extract as obtained in step (b) with n-hexane to obtain hexane soluble fraction and hexane insoluble residue,
d. triturating the hexane insoluble residue as obtained in step (c) with ethylacetate to obtain ethylacetate soluble fraction and ethylacetate insoluble residue,
e. suspending the ethylacetate insoluble residue as obtained in step (d) with water followed by extracting with n-butanol to obtain n-butanol soluble fraction,
f. isolating Apigenin, 4-methoxy-2',4'-dihydroxy chalcone), 7,4'-dihydroxy flavone, Luteolin, 7,3',4'-trihydroxy-flavone, Emodin, Nicotinic acid, Chrysophanol 1-O-β-Gentiobioside, Rhamnocathartin, Isovitexin or Apigenin 6c-glucoside from the n-butanol soluble fraction as obtained in step (e) by chromatographic methods,
g. solubilizing *Cassia* extract/fraction obtained in step (b) or in step (e) with surfactant mixture under stirring to obtain a nanoemulsion liquid preconcentrate formulation,
h. converting the emulsion liquid preconcentrate of step (g) into a solid system in situ to obtain the formulation by mixing with a solid carrier wherein the weight ratio of liquid in-situ nanoemulsion system to solid carrier is from 1:0.5 to 1:10.

8. The process as claimed in claim 7 wherein the alcohol is selected from ethanol or butanol.

9. The process as claimed in claim 7 wherein the surfactant mix consists of surfactant 20-40% w/w and co-surfactant 5-10% w/w.

10. The process as claimed in claim 7 wherein the solid carrier is selected from the group consisting of HPMC, soluplus, colloidal silica, hypermellose, and aerosil.

11. The formulation as claimed in claim 1 wherein the formulation has an effective osteoinductive and a skeletal preservation dose is reduced to 50 mg/kg in a butanolic fraction formulation from 250 mg/kg in an ethanolic extract.

12. The formulation as claimed in claim 1 wherein the formulation has an effective muscle protective dose is reduced to 50 mg/kg in a butanolic fraction formulation from 250 mg/kg in an ethanolic extract.

13. The formulation as claimed in claim 1 wherein the formulation is a bioactive fraction and the relative bioavailability (as shown by AUC) of apigenin 6-C-glucoside/isovitexin (biomarker) in the fraction is enhanced by more than 5 fold as compared to the extract.

14. The formulation of claim 5, wherein the one or more excipients are a polymer of a sugar selected from the group consisting of hypermellose, aeosil, HPMC, and soluplus and/or an inorganic material selected from the group consisting of colloidal silica, calcium carbonate, and calcium phosphate.

15. The formulation of claim 1, wherein the extract/bioactive fraction contains marker compounds Apigenin and Isovitexin.

16. The formulation of claim 15, wherein Apigenin is present in an amount of 0.0005% to 0.002% and Isovitexin is present in an amount of 0.0006% to 0.0008%.

* * * * *